(12) United States Patent
Coelho

(10) Patent No.: US 9,599,545 B2
(45) Date of Patent: Mar. 21, 2017

(54) METHOD FOR PURIFYING CERTAIN CELL POPULATIONS IN BLOOD OR BONE MARROW BY DEPLETING OTHERS

(71) Applicant: SynGen Inc., Sacramento, CA (US)

(72) Inventor: Philip H. Coelho, Sacramento, CA (US)

(73) Assignee: SynGen, Inc., Sacramento, CA (US)

( * ) Notice: Subject to any disclaimer, the term of this patent is extended or adjusted under 35 U.S.C. 154(b) by 537 days.

(21) Appl. No.: 14/256,946

(22) Filed: Apr. 19, 2014

(65) Prior Publication Data

US 2014/0212914 A1 Jul. 31, 2014

Related U.S. Application Data

(63) Continuation of application No. 13/634,520, filed as application No. PCT/US2011/028863 on Mar. 17, 2011, now Pat. No. 8,747,289.

(60) Provisional application No. 61/315,109, filed on Mar. 18, 2010, provisional application No. 61/436,964, filed on Jan. 27, 2011.

(51) Int. Cl.
*G01N 1/34* (2006.01)
*A61M 1/36* (2006.01)
*B04B 13/00* (2006.01)

(52) U.S. Cl.
CPC ............ *G01N 1/34* (2013.01); *A61M 1/3693* (2013.01); *A61M 1/3696* (2014.02); *A61M 2202/08* (2013.01); *A61M 2202/10* (2013.01); *B04B 2013/006* (2013.01)

(58) Field of Classification Search
CPC ............ A61M 1/3693; A61M 1/3696; A61M 1/0272; A61M 2202/08; A61M 2202/10; G01N 1/34; B04B 2013/006; B04B 7/10; B04B 7/14; B04B 7/16; B04B 11/04; B04B 11/06
See application file for complete search history.

(56) References Cited

U.S. PATENT DOCUMENTS

| | | | |
|---|---|---|---|
| 4,111,355 A | 9/1978 | Ishimaru | |
| 4,751,001 A | 6/1988 | Saunders | |
| 4,919,537 A | 4/1990 | Giebeler | |
| 5,704,889 A | 1/1998 | Hlavinka et al. | |
| 5,866,071 A | 2/1999 | Leu | |
| 6,143,183 A | 11/2000 | Wardwell et al. | |
| 6,315,706 B1 | 11/2001 | Unger et al. | |

(Continued)

FOREIGN PATENT DOCUMENTS

| CN | 2393550 Y | 8/2000 |
|---|---|---|
| CN | 1583213 A | 2/2005 |

(Continued)

*Primary Examiner* — David C Mellon
(74) *Attorney, Agent, or Firm* — Temmerman Law Office; Mathew J. Temmerman

(57) ABSTRACT

A method for purifying and harvesting certain cell populations in blood or bone marrow by depleting at least one of red blood cells, granulocytes, or platelets from a sample comprising blood, bone marrow, or stromal vascular fraction cells separated from adipose tissue is disclosed. The apparatus comprises a sterile, single use rigid, self-supporting cartridge within which the automated depletion, purification and harvesting of target cell populations occurs and all components may be distributed.

56 Claims, 37 Drawing Sheets

(56) References Cited

U.S. PATENT DOCUMENTS

2007/0151933 A1     7/2007   Coelho et al.
2008/0108120 A1     5/2008   Cho et al.

FOREIGN PATENT DOCUMENTS

| CN | 2721094 Y | 8/2005 | | |
|----|-----------|--------|---|---|
| CN | 1736497 A | 2/2006 | | |
| CN | 201182744 Y | 1/2009 | | |
| WO | WO 2007126357 A1 | * | 11/2007 | ........... B04B 5/0442 |

* cited by examiner

| Cell Types/source | | RBCs | GRNs | Lymphocytes | Monocytes | PLTs |
|---|---|---|---|---|---|---|
| Radius (μ) | | 3.5 | 6.0 | 5.0 | 9.0 | 1.5 |
| Unit Volume Ratio (R3) | | 42.90 | 216.00 | 125.00 | 729.00 | 3.38 |
| Numerical Ratio of Cell Population | NB | 1000.00 | 0.60 | 0.32 | .08 | 10.00 |
| | CB | 1000.00 | 1.20 | 0.64 | 0.16 | 20.00 |
| | BM | 1000.00 | 15.00 | 6.40 | 1.60 | 200.00 |
| Total Volume Ratio of Cell Population | NB | 42900 | 129.6 | 40.0 | 58.3 | 33.8 |
| | CB | 42900 | 259.2 | 80.0 | 116.6 | 67.5 |
| | BM | 42900 | 3240 | 800 | 1166 | 675 |
| % of Total Volume of Concentrated Cells | NB | 99.39 | 0.30 | 0.09 | 0.14 | 0.08 |
| | CB | 98.79 | 0.60 | 0.18 | 0.27 | 2.39 |
| | BM | 87.94 | 6.64 | 1.64 | 2.39 | 1.38 |

Figure 3: Proportionate Volume of Cell Populations After Centrifugation

| Cell Types | | RBCs | GRNs | MNCs | PLTs |
|---|---|---|---|---|---|
| 50ml | NB | 22.36 | 0.07 | 0.05 | 0.02 |
| | CB | 22.23 | 0.14 | 0.10 | 0.04 |
| | BM | 19.79 | 1.49 | 0.90 | 0.09 |
| 100 ml | NB | 44.73 | 0.14 | 0.10 | 0.04 |
| | CB | 44.46 | 0.27 | 0.20 | 0.07 |
| | BM | 39.57 | 2.99 | 1.80 | 0.17 |
| 150ml | NB | 67.09 | 0.20 | 0.16 | 0.05 |
| | CB | 66.68 | 0.41 | 0.30 | 0.11 |
| | BM | 59.36 | 4.48 | 2.70 | 0.07 |
| 200ml | NB | 89.45 | 0.27 | 0.21 | 0.07 |
| | CB | 88.91 | 0.54 | 0.41 | 0.14 |
| | BM | 79.15 | 5.98 | 3.60 | 0.34 |

Figure 4: Volume of Cells in Various Volumes of Anti Coagulated Blood

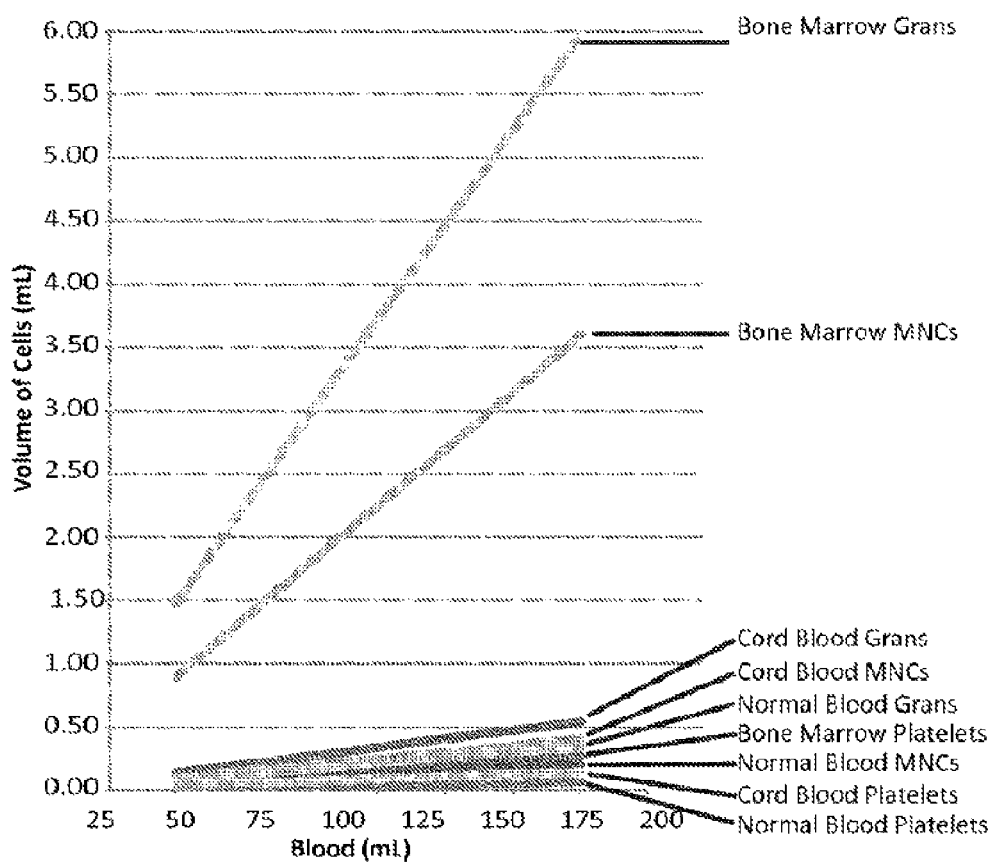
Figure 5: Volume of Anti Coagulated Blood Versus Volume of Centrifuged Cell Populations

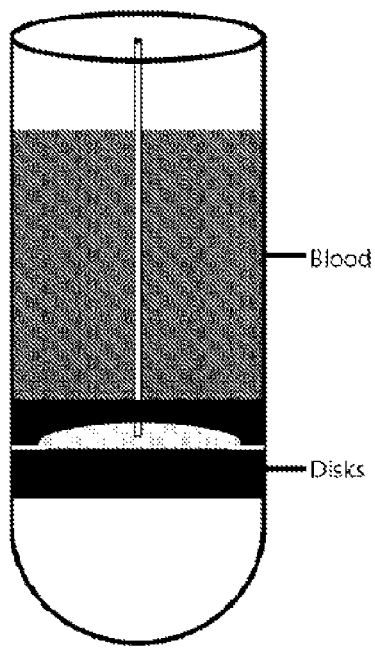
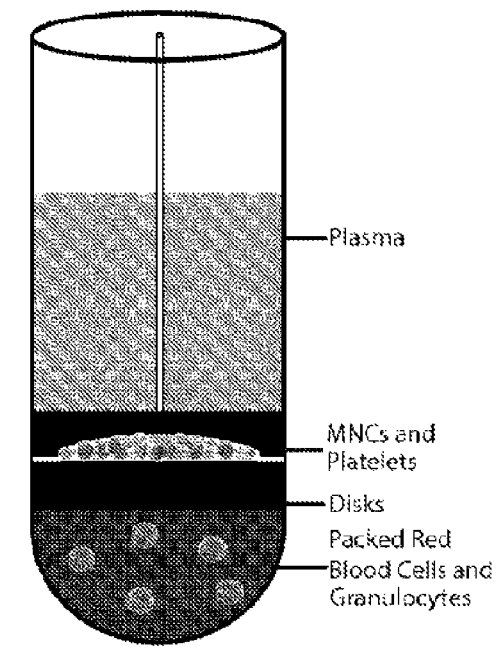
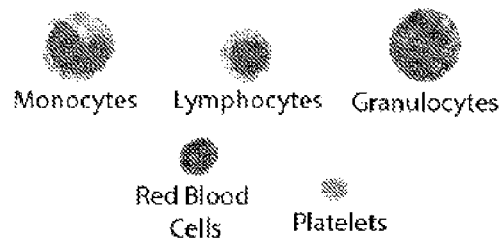
Figure 8

| (ESR 95% limits) | Age (years) | | |
|---|---|---|---|
| | 20 | 55 | 90 |
| Men | 10 mm/hr | 14 mm/hr | 19 mm/hr |
| Women | 15 mm/hr | 21 mm/hr | 23 mm/hr |

Figure 9: Adult ESR reference ranges

SCR-1000 cartridge design leapfrogs earlier solutions
Thermogenesis
AXP or MXP
Processes 35-150 mL
BioSafe
Sepax
Processes 35-250 mL
Synergenesis
SCR-1000
Processes 20-250 mL
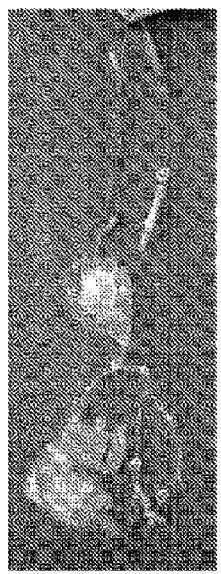
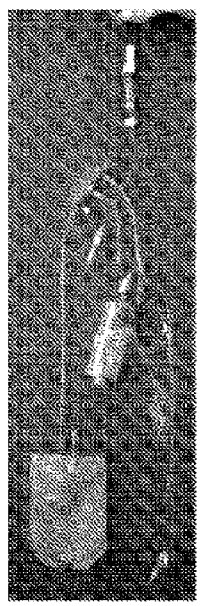
• Precision injection molded construction
• Loads in 5 seconds
• Minimal training for optimal use
•Cell purity regulated by four infrared sensors
26 Glue Joints          24 Glue Joints          6 Glue Joints
Figure 11

METHOD FOR PURIFYING CERTAIN CELL POPULATIONS IN BLOOD OR BONE MARROW BY DEPLETING OTHERS

RELATED APPLICATIONS

The present application is a continuation of U.S. nonprovisional application Ser. No. 13/634520, filed Sep. 12, 2012, granted Jun. 10, 2014 as U.S. Pat. No. 8,747,289 B2, and which is a 35 U.S.C §371 application to PCT application No. PCT/US2011/028863, filed Mar. 17, 2011, which claims the benefit of from the United States provisional application having Ser. No. 61/315,109, filed Mar. 18, 2010, and from United States provisional application having Ser. No. 61/436,964, filed Jan. 27, 2011. The entire contents of each of these applications are hereby incorporated by reference.

BACKGROUND

Field of the Invention

The present invention relates to a cell separation system, and in particular to a system for depleting certain blood components from normal blood, placental/umbilical cord blood, bone marrow, or stromal vascular fraction (SVF) cells once separated from adipose tissue.

Background of the Invention

Normal human blood generally comprises platelets ("PLTs"), plasma, red blood cells ("RBCs"), white blood cells ("WBCs"), and, in very small quantities, stem and progenitor cells (SPCs). On average (known to vary among individuals and, over time, within the same individual) RBCs make up approximately 99.9% of the number of an individual's total blood cells and account for approximately 45% of an individual's total blood volume. RBCs serve a vital function as the principal means of delivering oxygen to the body tissues. Nearly all of the remainder of an individual's blood volume is made up of plasma, a non-cell liquid component of blood accounting for approximately 55% of the total blood volume and in which all blood cells are suspended.

Thus, over 99% by volume of normal blood is made up of plasma and RBCs. The remaining approximately <0.6% by volume of normal blood consists of all other blood cell types and PLTs. PLTs are small, irregularly shaped anuclear cells that outnumber the WBCs by a factor of ~10. PLTs play a fundamental role in wound care by stopping bleeding and releasing a multitude of growth factors that repair and regenerate damaged tissue.

The next most prevalent blood cells are WBCs, making up by number only about one tenth of one percent of the total cells in a typical blood sample. However, WBCs are critical to the body's immune system and defend the body against both infectious disease and foreign materials. The WBCs may be further divided into smaller subgroups. The largest such subgroup is granulocytes (GRNs), making up approximately 60% of all WBCs, and the other approximately 40% being mononuclear cells (MNCs). Throughout this application, the use of the term WBC may indicate a reference to exclusively GRNs, exclusively MNCs, or some combination of both.

MNCs can further be broken down into lymphocytes and monocytes, but may collectively be referred to as MNCs due to the presence in each cell of a single round nucleus. MNCs are critical elements of the immune system, comprising T cells, B cells and NK cells that migrate to sites of infection in body tissue and then divide and differentiate into macrophages and dendritic cells to elicit an immune response. Finally, the MNCs themselves can be further divided into even smaller subclasses—including extremely small quantities of multipotent hematopoietic (blood forming) stem and progenitor cells and mesenchymal (bone, fat, cartilage, muscle and skin forming) stem and progenitor cells, both critical to human health. Another source of MNCs are the stromal vascular fraction cells (SVFCs) that have been separated from adipocytes removed from individuals during liposuction.

Samples of normal blood, placental/umbilical cord blood or bone marrow are drawn in excess of 25 million times per year in the industrial world. Because the samples are generally taken either as a part of research into treatment of disease or for direct clinical treatment, the blood cells most often isolated are WBCs, followed by MNCs. MNCs include all the stem and progenitor cells, and approximately 40% of the critically important immune cells. Thus the cells most often in demand represent only a very small fraction of the cells drawn for a typical sample.

Thus if a relatively purified population of cells containing essentially all the stem and progenitor cells (SPCs) and depleted of substantially all the RBCs is desired, there is a need to separate the components of blood or bone marrow described above so as to isolate the WBCs or, if more purity is desired, the MNCs. This need for consistent, effective processes to separate these cell populations and harvest the target cells is especially pressing due to the increasing demand for SPCs for research, clinical trials, and point of care medical practices.

The interest in and research conducted on SPCs is staggering. As of November 2010 over 100,800 stem cell research articles have been published worldwide. There are currently at least 7,000 principle researchers focused on SPCs worldwide. In the United States alone there are some 300 stem cell research centers and approximately 10,000 individual labs. As a result of this extensive research has 199 clinical trials with cord blood stem cells, 34 clinical trials using adipose tissue, and 1,405 clinical trials using bone marrow stem cells are now underway according to clinical-trials.gov, the NIH website.

Description of Related Art

Conventional methods of isolating and harvesting certain cell types from a whole blood or bone marrow aspirate sample generally involve centrifugation of the sample. During centrifugation, populations of cells tend to migrate to a relative position along the axis of lesser to greater acceleration according to their density, and concentrate in layers, displacing other higher and lower density cell types and plasma during the process.

FIG. 1 shows the density and average diameter of various cell types found in human blood. The physical differences between different cell types are important when the blood is centrifuged. When the blood is centrifuged the cells begin to move to new locations at velocities that are in accordance with many fluid dynamic factors, including Stokes Law. The fact that all cells retain a slight negative charge militates against direct cell-membrane-to-cell-membrane contact. In an environment comprising mainly plasma, with relatively few cells, the larger the cell, the more rapidly it travels. However as the concentration of cells rises, the effect of cell charge begins to substantially determine cell velocity.

However, in all cases, the denser the cell, the lower in the container (that is, further from the axis of centrifuge rotation) it will ultimately migrate to and settle. Thus, as shown in FIG. 2, the densest cells, RBCs (having a density between 1.08 and 1.12), will migrate to the bottom of the container being centrifuged. Within the RBC layer the nucleated red blood cells (which exist in both cord blood and bone marrow but not in normal blood) will be at the top of the red cell fraction. On top of the RBCs will be the GRNs (density 1.07-1.11), then, in order moving closer to the axis of rotation in the container, the lymphocytes (density 1.05-1.09), monocytes (density 1.045-1.0750) and the PLTs (1.03-1.065). It is known that the SPCs have a density closest to monocytes and lymphocytes and thus can be captured if those more numerous cells are captured. By taking advantage of the known strata that form under certain conditions, harvesting of one type of cell can be facilitated through the harvesting of only its strata. FIG. 2 also shows the relative frequency of the blood cell types in typical samples of normal blood, cord blood and bone marrow, and finally shows that there is some overlap in cell populations organized by density, as will be discussed below.

While creating the stratified cell layers generally requires nothing more than the application of high G forces over a set amount of time, precisely removing a specific layer of cells is problematic. To illustrate the rarity and small volume of certain cell populations in a given sample, FIGS. 3, 4, and 5 detail the respective average volumes of each cell population in normal blood (NB), cord blood (CB) and bone marrow (BM) after centrifugation and stratification.

FIGS. 3 and 4 illustrate that the vast majority of cells are RBCs, while FIG. 5 shows clearly that the volumes of non-RBC cellular blood components are so small that even with a 200 ml sample of cord blood the total volume of all GRNs (top line), MNCs (middle line) and PLTs (lower line) is about 1 mL. In cord blood fewer than 1 out of every 1,000 blood cells (approximately 0.08% of total cells) is an MNC. In a cord blood sample including 10,000 RBCs, one would expect to find 40-200 PLTs, 3-6 MNCs, and 5-10 granulocytes.

As explained, the vast majority of blood by both number of cells and by volume is made up of cells other than WBCs. Because of the scarcity of these WBCs and their residence within liquid solutions populated by enormous numbers of RBCs, current methods to isolate WBCs are (A) labor and time intensive, requiring excellent laboratory technique, (B) typically cannot be accomplished in a sterile environment, (C) typically have only between a 50-75% efficiency rate in capturing WBCs (a loss of 25% to 50% of the WBCs), and (D) involve processes that may adversely affect cell function. Given the typically small size of blood samples and the fact that SPCs are exceedingly rare in normal blood, there may be no SPCs at all in a typical harvest of the WBCs from normal blood and, although SPCs are more numerous in cord blood than in normal blood, they are still rare in cord blood.

To further illustrate how difficult it is to obtain WBCs from normal blood, a diagrammatic 50 ml test tube normally used in conventional manual blood component separation methods is shown in FIG. 6. These tubes are typically 28 mm in width. After centrifugation the separated blood components are the plasma (top) and the RBCs (bottom) and a nearly invisible thin layer called a "buffy coat" disposed in between (exaggerated in size in FIG. 6 for purposes of illustration). This "buffy coat" contains nearly all the WBCs, SPCs and PLTs.

Although several semi-automated systems for harvesting WBCs from whole blood are currently being marketed, their advantage in cell recovery efficiency relative to manual methods is not significant, and their market penetration is small. The prevalent current methods for isolating and capturing WBCs within a blood or bone marrow sample employ two manual processing technologies (A) the density gradient granules method and (B) the density gradient disk method. For diagnostic or research purposes, it is estimated that ninety-nine times out of a hundred when WBCs are isolated from blood or bone marrow they are isolated using these technologies. Both typically utilize cylindrical tubes for the process, and both rely on the careful manipulation of densities. For example, if the goal is to isolate MNCs, many thousands of tiny granules or a disk (of slightly smaller diameter than the tube inner diameter) with a density of approximately 1.08 are placed in the tube. This specific density value is chosen as it is equidistant between the median densities of GRNs and lymphocytes (see FIG. 2). In order to function correctly, both these technologies require that the blood sample first be diluted with an amount of buffer equal to 2 to 4 times the blood volume.

Referring first to the granule method, after the buffered blood sample is mixed with the granules in the test tube, centrifugation is initiated. During centrifugation, the density of the granules causes them to coalesce such that they divide the RBCs/GRNs from the MNCs/PLTs. FIG. 7 illustrates this process with Ficoll density gradient granules dividing the MNCs from the RBCs/GRNs.

The method of using density gradient disks is very similar and is illustrated in FIG. 8. Here, the disks of density 1.08 migrate under centrifugation to the interface between lymphocytes and GRN. However, most density gradient disks contain one feature not found in the granules above: they comprise a cavity between the upper and lower disks where it is expected the MNCs will settle, thus somewhat simplifying the step of harvesting of MNCs via a flexible tube that travels between the cavity and the top of the tube.

These manual methods for isolating and capturing MNCs from a blood sample require patience and excellent manual dexterity. These methods typically require 1½ to 2 hours to perform, and even with best practices, recovery of MNCs is often less than 60%. Thus the manual methods commonly employed for isolating and capturing MNCs within a blood sample are less than optimal in terms of precision and speed because of numerous limitations in this technology.

First, density gradient solutions achieve isolation of a population of WBCs from blood or bone marrow by relying on only one physical factor—density. Once the centrifugation begins, the density gradient medium moves to a position where it is buoyant in the cell solution and stops. Typically, this migration of the cell populations to their final positions occurs during an acceleration and duration that are both fixed, and thus rarely optimal for an individual blood sample.

Essentially the WBC or MNC harvesting efficiency of both density gradient technologies is limited by the need to aim at the center of the gap between the median density bell curves of the granulocytes and the lymphocytes (i.e., 1.08), as mentioned above with regard to FIG. 2. As FIG. 2 makes clear, this fixed density clearly does not exclude all the granulocytes or even all RBCs and does, in fact, discard some of the desired lymphocytes.

This simplistic approach also does not accommodate the fact that even in normally healthy people, there exists significant variation in the number and density of cells of each type and the sedimentation rates among samples may differ by as much as an order of magnitude. Further, if the patient has certain diseases the variation in the relative cell populations and the sedimentation rates of the cells can be much greater—up to two orders of magnitude. Consequently, these primitive WBC or MNC isolation technologies are rarely optimal for any specific sample of blood.

The best way to conceive of the severity of this limitation is to understand that the cells in a sample of blood, evenly distributed throughout the volume prior to centrifugation, begin a race to a new location when centrifugation begins. The efficiency of the WBC or MNC isolation technology depends upon how precisely all the WBCs wind up at the same strata at the end of the race—and how well the technician can extract the WBCs from this location with a pipette at normal 1G conditions where the cells will begin to remix with only the slightest motion of the container, or the slightest motion of the pipette tip.

Scientists have long studied the rate at which RBCs from normal blood migrate down a container under 1G conditions. This measurement is called the erythrocyte sedimentation rate, or ESR. Although the centrifugal acceleration used in conventional MNC isolation processes accelerate this rate of sedimentation, they do not change the percentage variation of the sedimentation rates of the different cell types. Further, as RBCs are more than 1000 times as numerous as WBCs and 2000 times as numerous as MNCs, and all the cells maintain a slight negative charge, it is the RBC migration that most effects isolating the WBC populations.

The ESR (measured in millimeters per hour—mm/hour) in adults of various age are shown in FIG. 9. In children, normal values of ESR have been found to be 1 to 2 mm/hour at birth, rising to 4 mm/hour 8 days after delivery, and then to 17 mm/hour by day 14 (a change of more than an order of magnitude in less than two weeks). The ESR is so variable that it is used to diagnose malignant diseases, such as multiple-myeloma, various auto-immune diseases such as rheumatoid arthritis, and chronic kidney diseases wherein the ESR may exceed 100 mm/hour, five times that of a normal adult.

Further, it is noted that WBCs at the bottom of a container can only move upward to join those descending from the top of the container as a result of being buoyed up on the ascending plasma displaced by the descending RBCs. Note that the very small number of WBCs in a solution must negotiate their path upwards against the flow of RBCs, a thousand times more numerous, moving in the opposite direction through the same vertical channel. Further, as the acceleration and duration of the centrifuge is programmed at the start of the run, a duration that is satisfactory to relocate all the cells within a specific sample may be insufficient for many other blood samples in that most of the RBCs may not have arrived at the bottom of the tube and thus many of the target WBCs may not have been buoyed up to the "buffy-coat" strata by the ascending plasma. As this process takes place in a closed centrifuge within a rapidly spinning rotor, the operator is unable to observe the actual motion of the cells.

There is thus a need for a system, which optically tracks, in real time, the migration of cell populations within each individual blood sample during centrifugation. Such a system would allow each individual blood sample to be custom processed according to the specific size and density of that blood sample's constituent cell populations. This improved solution should also greatly increase the harvesting efficiency of target WBC or MNC cell populations.

A further drawback to density gradient mediums is that they require buffers, which occupy most of the volume of a given harvest tube, minimizing the volume of blood from which WBCs are to be harvested. A buffer often occupies 70% to 90% of the 50 ml volume of a typical harvest tube, leaving space for only 5 to 15 ml of blood. Consequently, a technician who needs to harvest WBCs from 100 ml of blood must employ 7 to 20 test tubes—further increasing the labor required to accomplish the goal. Additionally, in order to achieve adequate purity from contaminants in the final WBC population, the granular density gradient mediums and the buffers will need to be washed out, inevitably causing a further loss of target cells.

There is thus a need for a means for depleting undesired cells from a blood or bone marrow sample, which does not require voluminous density gradient mediums or buffers. The means may optionally allow the harvest of WBCs from larger volume samples, further increasing the number of constituent cells that may be recovered for diagnostic or clinical use.

A third drawback to the density gradient based blood separation methods described above is that the parallel vertical walls of a density gradient harvest tube do not assist the WBCs rising during centrifugation to lie atop the RBCs. The density gradient harvest test tubes in conventional systems have vertical parallel walls meaning that during centrifugation all the cells either fall or rise vertically along the axis of the tube. As described above, each ascending WBC must negotiate thousands of RBCs moving in the opposite direction. The harvest test tube's parallel vertical walls provide no lateral motion to descending RBCs and ascending WBCs that could assist the rise of the WBCs during centrifugation. As a result a significant portion of the WBCs that began the spin cycle in the bottom of the tube may not rise to the harvest "buffy coat" layer during the chosen centrifugation regimen.

There is thus a need to overcome the entrapment of WBCs at the bottom of the test tube through utilization of a funnel-shaped harvest chamber that radically narrows at the bottom, such that most of the descending RBCs are forced to the center, enhancing eddy currents led by the lightest of the RBCs ascending to the top of the RBC volume. In turn these eddy currents assist the ascension of the much less numerous but more buoyant WBCs.

A fourth drawback to the density gradient based separation methods is the constant large cross sectional area of the density gradient harvest test tube at the location where the MNCs are harvested manually at 1 G.

Because the walls of a standard 50 ml density gradient harvest tube are a fixed ~28 mm apart, the very small volume of MNCs from a 10 ml peripheral blood sample (~0.028 ml) are spread across the entire cross sectional area of the tube (~615 mm$^2$) in a thin layer (~0.023 mm) which is nearly invisible. Because of this broad cross sectional area and the resulting thin layer of MNCs, the stratifying effects of the density differences between cell populations are miniscule. Consequently, harvesting the MNCs at 1 G requires a highly trained technician to slowly and carefully insert a pipette tip into this very thin layer of cells that floats between the density gradient (below) and plasma (above) and then gently apply a suction to draw the MNCs up into the pipette. However, the very small density variations between cell populations, when not magnified by substantial centrifugal forces, and the large cross sectional area of the tube conspire to keep the MNCs/PLTs essentially all in the same thin vertical layer. Consequently, no amount of care during this manual suction process prevents the roiling of the MNC/PLT layer and the density gradient media so a loss of MNCs and substantial contamination of the cells by the density gradient granules ensues. It is thus not uncommon to lose ~25-40% of the MNCs during this procedure.

There is thus a need to avoid losses during the harvest of MNCs by depleting RBCs and most of the GRNs through the narrow cross sectional area of a funnel exit while substantial centrifugation maintains the integrity and purity of the cell strata and elongates them vertically as they descend down the tapered funnel.

A fifth drawback to conventional density gradient granule based systems is due to the direct contact between the density gradient granules and the cells. The extensive direct contact between these granules and the cells to be harvested has been reported to damage the cell function due to a form of toxicity. For example, Yuhan Chang, et al recently reported in "*The Efficiency of Percoll and Ficoll Density Gradient Media in the Isolation of Marrow Derived Human Mesenchymal Stem Cells with Osteogenic Potential*" (Chang Gung Med J 2009; 32:264-75) that when cytoxicity tests were run on CFU-Fs (passage one) by culturing with a mixture of control medium and Percoll or Ficoll in serial dilutions to assess the growth-inhibitory or cytotoxic effects of these two gradient media, the CFU-Fs exhibited greater cell death as the ratio of gradient medium increased in both groups.

There is thus a need to provide for the depletion of RBCs, or RBCs and GRNs, or RBCs, GRNs and PLTs, or RBCs, GRNs and MNCs, without requiring the addition of density gradient granules or any other foreign matter that may alter or damage cell function.

A sixth drawback of conventional blood separation methods, with or without density gradient granules, is the probability that significant numbers of RBCs may remain in the final product due to the variability in technician competence and the ease of inadvertently remixing the cells at 1 G. Several recent studies have highlighted the importance of minimizing RBC contamination because such contamination decreases the efficacy of medical treatments using these MNCs.

Examples of these mal effects of RBC contamination abound, for example see "*Red Blood Cell Contamination of the Final Cell Product Impairs the Efficacy of Autologous Bone Marrow Mononuclear Cell Therapy*," Assmus et al., Journal of the American College of Cardiology, 55.13, 2010, wherein it is disclosed that contaminating RBCs affect the functionality of isolated BMCs and determine the extent of left ventricular ejection fraction recovery after intracoronary BMC infusion in patients with acute myocardial infarction. See also, "*Packed Red Blood Cells Suppress T-Cell Proliferation Through a Process Involving Cell-Cell Contact*," Bernard et al., The Journal of Trauma, Injury, Infection, and Critical Care, 69.2, August 2010, wherein it is disclosed that stored RBCs exert a potent inhibitory effect on T-cell proliferation, and it is likely that similar suppression of T-cell proliferation could occur in vivo after blood transfusion and may be a major contributor to transfusion related immunomodulation.

There is thus a need to provide for the greater and more predictable depletion of RBCs, GRNs and, possibly, PLTs from a collected sample of normal or cord blood, bone marrow or SVF cells separated from adipose tissue in order to recover a more purified solution containing SPCs.

The few commercially available systems that have automated this cell separation and depletion process (such as the Hemonetics V50, the Cobe Spectra, the Sepax System by Biosafe SA of Switzerland, and the Thermogenesis AXP by Thermogenesis Corp. of California) also have substantial drawbacks and have not achieved improved recoveries of purified WBCs relative to the conventional manual methods. An additional drawback is that these commercially available automated systems require expensive capital equipment in order to operate. These automated devices cost tens of thousands of dollars and occupy substantial laboratory space if significant production of units of purified WBCs are required—such as with cord blood stem cell banks that may process 40 to 200 units per day. FIG. 10 illustrates the costs of processing four units of blood with two prior art systems and with the current system.

A second drawback of the currently commercially available automated systems is that they require complicated, expensive, difficult to manufacture single use disposable bag sets linked together with substantial tubing to process the cells, as shown in FIG. 11. These bag sets take approximately five minutes to correctly load into their dedicated devices and to ready the system to process the blood or bone marrow. These prior art bag sets are complex and costly to manufacture. As shown in FIG. 11 these prior art bag sets require more than 20 individually formed glue joints.

There is thus a need for a simpler, less expensive, faster and easier to use automated system that is also able to achieve higher recoveries of WBCs with less contamination by RBCs. There is further a need for a system that employs a simple, inexpensive to manufacture single-use disposable processing container, which does not require multiple bags and complex connecting tubing.

FIG. 12 illustrates the simplicity of the current invention in that it provides an all-in-one cylindrical cartridge in which all cell processing occurs and in which all components related to cell stratification and depletion are disposed. In as few as one or two seconds this cartridge may lock onto the top of a dedicated cylindrical control module and be ready for insertion into a centrifuge cup. The control module contains optical and gravitational sensing means as well as means for controlling the activity in the cartridge.

This all in one cartridge benefits from the manufacturing precision of injection molding and is much simpler and labor efficient to construct than conventional processing disposables for prior art automated systems typically comprising multiple bag sets and complicated connecting tubing connected thereto.

It is thus a first objective of the present invention to optically track the migration of the cell populations for each individual blood sample and to then deplete certain cell types by diverting them into a secondary and separate compartment within the same cartridge during centrifugation.

It is a second objective of the present invention to provide for the selective depletion of substantially all unwanted cell types while not requiring volume consuming density gradient mediums or buffers.

It is a third objective of the present invention to provide a rigid funnel shaped harvest chamber that is substantially narrower at its bottom portion such that descending RBCs are forced to the center of the funnel, thereby enhancing vertical eddy currents led by the lightest of the RBCs ascending to the top of the red cell volume which assists the ascension of the much less numerous but more buoyant WBCs to the initial WBC stratification and concentration level.

It is a fourth objective of the present invention to provide an all-in-one cartridge in which all cell processing occurs and in which all components related to cell stratification and depletion are located at the completion of the centrifugation. The cartridge may be easily, quickly and removably locked to a control module that, under centrifugation, relies on its own strength for support rather than a support structure in which it is nested. This cartridge preferably comprises at least three rigid compartments: (1) The RBC compartment into which the bulk RBCs and, at operator discretion, unwanted GRNs are directed; (2) the stem cell (SC) compartment into which the targeted WBCs are directed which may include, at operator discretion, GRNs, lymphocytes, monocytes, SPCs and/or platelets; and (3) the harvest funnel which initially contains the entire sample of blood or bone marrow and retains, after processing, any excess plasma.

It is a fifth objective of the present invention to create a layer of WBCs within a funnel that, when urged downwards by centrifugal force, encounter a portion of the funnel of decreasing diameter, thereby causing said WBC layer to increase in vertical thickness.

It is a sixth objective of the present invention to provide a means for stratifying a blood sample into RBCs, GRNs, MNCs, PLTs and plasma, and for precisely opening and closing certain valves at the interface between certain cell layers.

It is a seventh objective of the present invention to provide a means of harvesting a higher percentage of the WBCs while simultaneously depleting a higher percentage of RBCs than is obtainable using conventional manual or automated systems and without the requirement of RBC sedimentation agents such as hetastarch.

It is an eighth objective of the present invention to provide the above seven objectives at a reduced cost as compared to conventional manual and automated systems currently in place.

These and other objectives, advantages, features, and aspects of the present invention will become apparent as the following description proceeds. To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed

SUMMARY OF THE INVENTION

The present application presents to a method and device for depleting RBCs from a blood sample and, in some circumstances, depleting GRNs, and, in other circumstances, PLTs, the method comprising the centrifugation of a cartridge based holder and separator of cell solutions. FIG. 13 shows a simple schematic overview of the process described herein. The present invention selectively depletes substantially all unwanted RBCs, and, at the discretion of the operator, also depletes certain WBCs (preferably GRNs) and also, at the discretion of the operator, depletes PLTs from a blood or bone marrow sample so as to optimally isolate and then harvest purified MNCs. The invention in the preferred embodiment comprises a single use hard plastic cartridge in which all processing occurs and in which all cell populations, PLTs, and plasma may be distributed during centrifugation. The invention eliminates the need for density gradient granules or disks. The invention also eliminates the need for fragile thin film plastic bag sets and their complicated and wasteful interconnecting tubing, which leads to leaks at the many glued joints, and which unavoidably traps MNCs and SPCs that cannot subsequently be recovered. The invention further provides an easy-to-use locking cartridge comprising an interior funnel with a precisely narrowing cross section to optimize the flow of cells within a gravity-well and to vertically stratify cell populations.

As shown in FIG. 13, in use, at a high G-force, the WBCs may first be stratified out from a sample of peripheral or umbilical cord blood, bone marrow or solution of SVF cells removed from adipose tissue. Then at a second, lower G force, the device and method allow the centrifugal force to urge the cells away from the axis of rotation and direct the RBCs from the bottom of the funnel to a contained compartment. As the stratified WBCs enter the space of decreasing diameter formerly occupied by the departing RBCs, a disk of WBCs and MNCs of decreasing radius and increasing vertical thickness is formed.

By removing RBCs during centrifugation, the WBC layer between the RBC layer and the plasma layer moves down into this narrow portion of the funnel to the point that the WBCs and MNCs are at the top section of the narrowing funnel. Subsequently as the red cells continue to be removed, either to the RBC depletion compartment or to precede the WBCs to be captured into the SC compartment the stratified layers are vertically elongated, thereby facilitating the removal of only the desired cell types.

It is to be understood that funnel tips of varying circumferences and geometries, as shown in FIG. 14, may be employed. These different circumferences and geometries alter the flow rate and cell density, and subsequently the optical readings of the infrared sensors, as the cells move towards the funnel exit.

In the preferred embodiment an optical sensing system identifies each type of cell population as they exit the funnel. The optical sensing system is in communication with one or more valve means for directing and controlling the flow of certain populations of cells to one of two locations. For instance, and as illustrated in FIG. 13, as the stratified layer of WBCs passes the optical sensing system, the WBCs may be directed to a secondary SC recovery compartment within the disposable cartridge. The WBCs may then be urged by the pressure of the fluid and cells behind/above the WBCS to move initially perpendicular to the axis of rotation and then upwards toward the axis of rotation into a standpipe in the SC recovery compartment.

The present invention may further comprise a means to track the gravitational field over time and to provide data critical to both the depletion of the RBCs and, optionally, GRNs and/or PLTs from the sample.

BRIEF DESCRIPTION OF THE FIGURES

The foregoing aspects and many of the attendant advantages of the invention will become more readily appreciated as the same becomes better understood by reference to the following detailed description, when taken in conjunction with the attached charts and figures, wherein:

FIG. 3 is a table of the proportionate volume of cell populations after centrifugation;

FIG. 4 is a table of the volume of cells in various volumes of anti-coagulated blood;

FIG. 5 is a plot of the volume of anti-coagulated blood versus the volume of centrifuged cell populations;

FIG. 8 is a diagram showing how human blood separates when centrifuged with blood separation discs in a standard test tube;

FIG. 9 is a table of ESR values of average men and women of different ages.

FIG. 11 is a drawing showing the relative complexity of the disposable component of prior art blood separation systems and the current invention;

DETAILED DESCRIPTION OF THE INVENTION

The following description is presented to enable a person of ordinary skill in the art to make and use various aspects and examples of the present invention. Descriptions of specific materials, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described and shown, but is to be accorded the scope consistent with the appended claims.

The applicant discloses a method and device for depleting RBCs from a blood sample and, in some circumstances, depleting a particular GRN, and, in other circumstances, PLTs. The preferred embodiment of the present invention accomplishes this substantial depletion through centrifugation so as to optimally isolate and then harvest WBCs including substantially all the SPCs.

Figure 1:
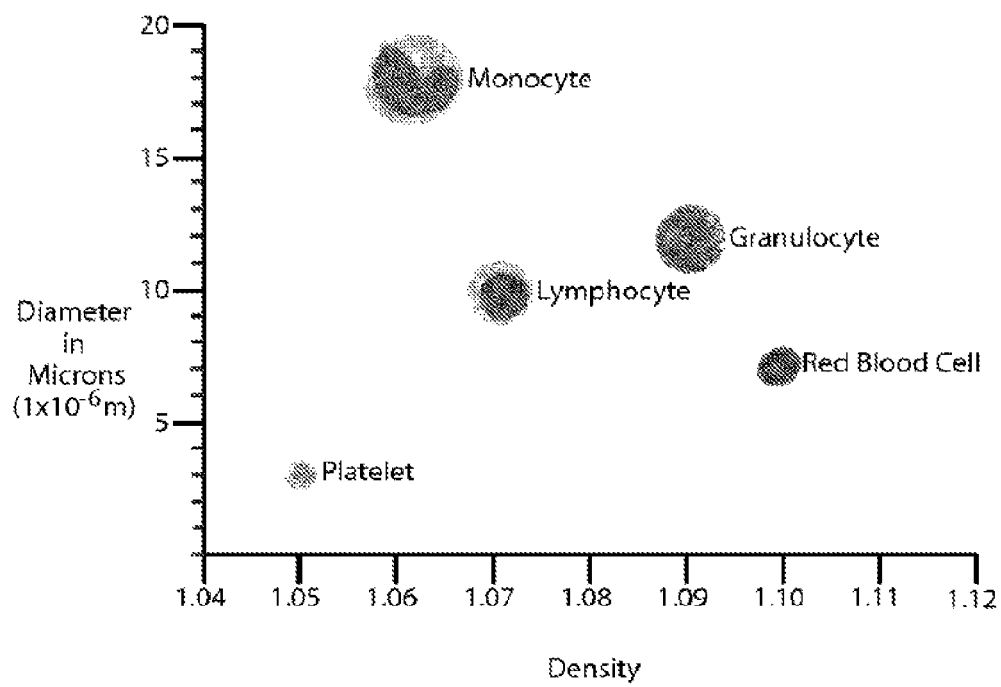
FIG. 1 is a plot of the density and average diameter of various cell types found in human blood.
Figure 2:
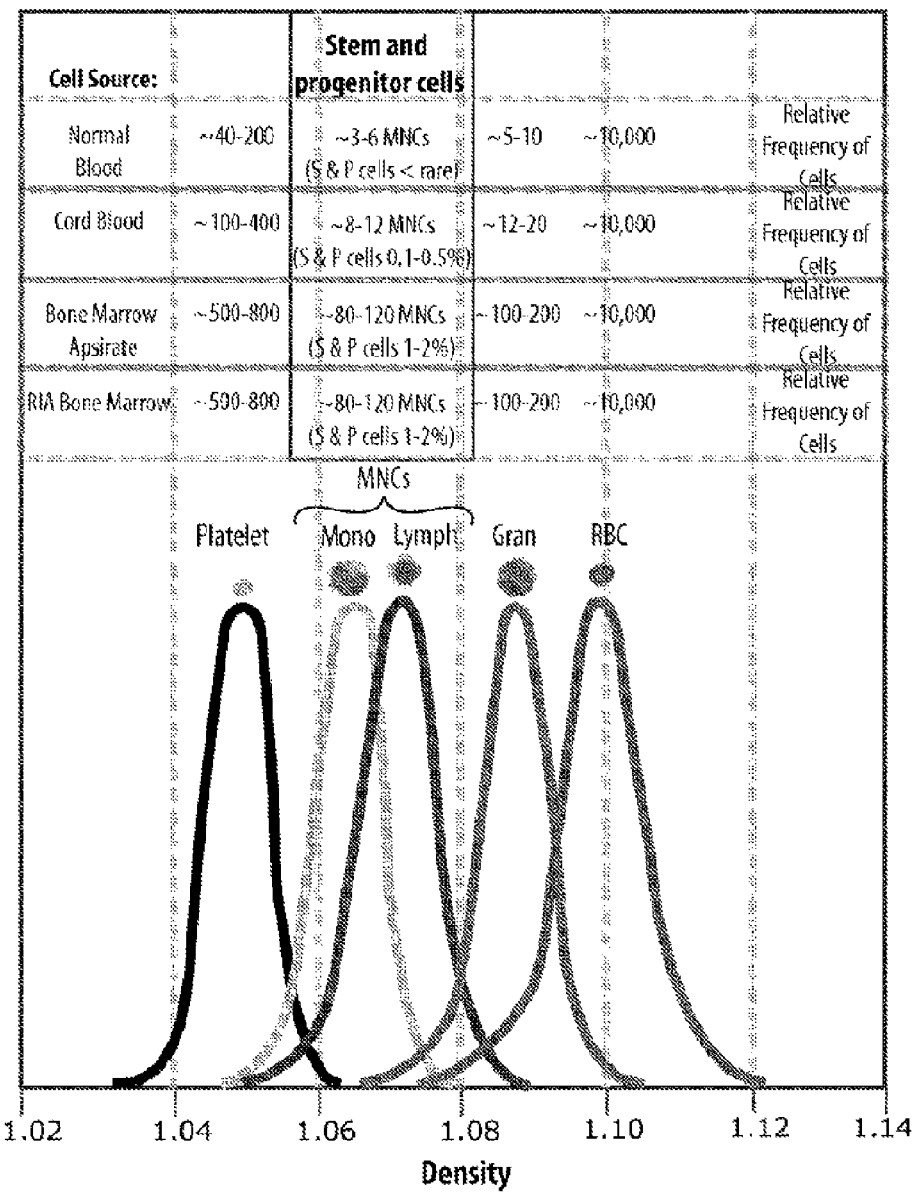
FIG. 2 is a plot showing the different densities of various cell types found in human blood.
Figure 6:
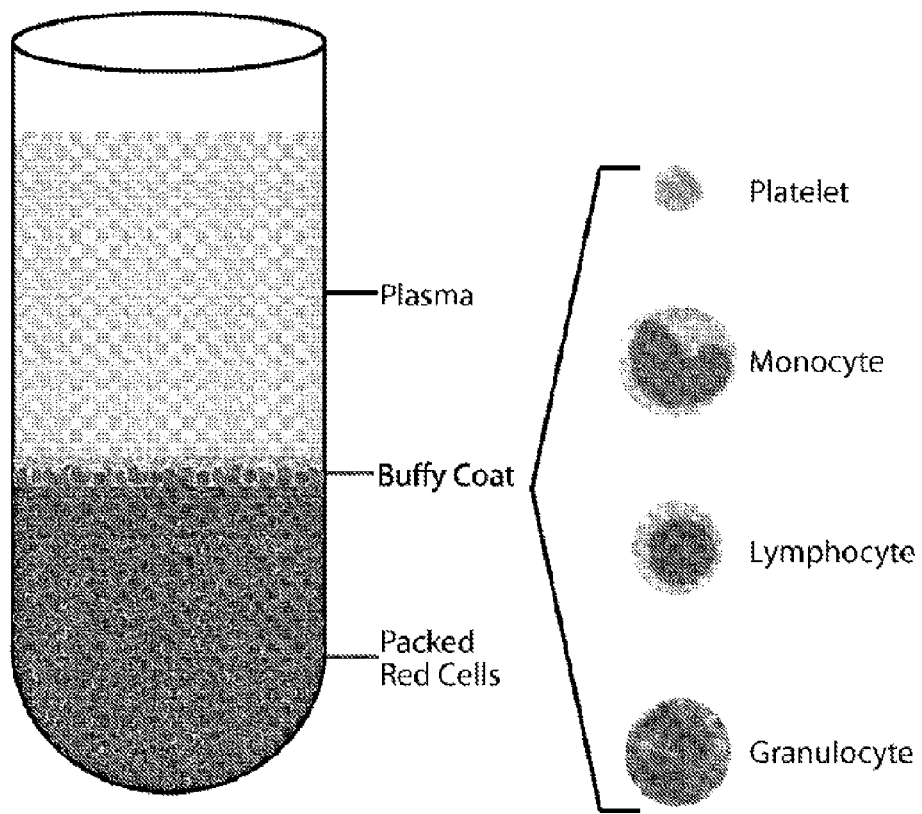
FIG. 6 is a diagram showing the layers into which human blood separates during centrifugation in a standard test tube.
Figure 7:
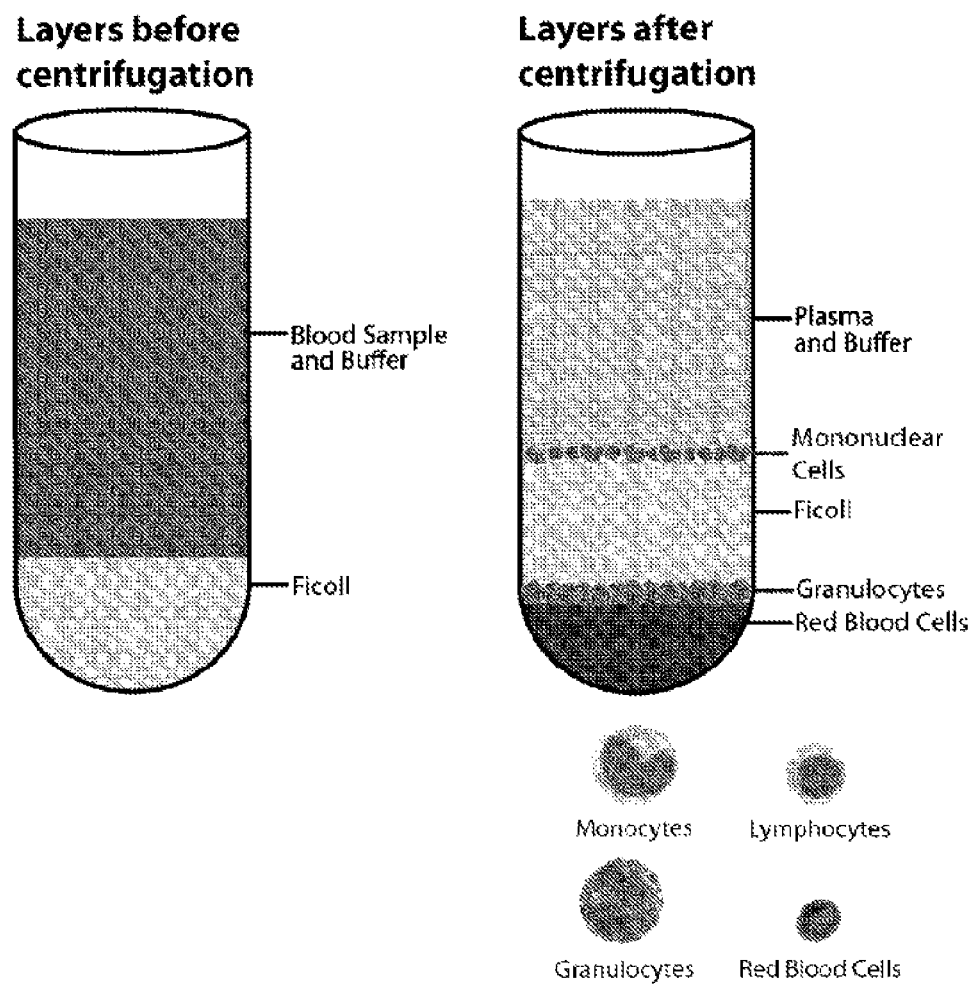
FIG. 7 is a diagram showing the layers into which a mixture of human blood and a Ficoll additive separate after centrifugation.
Figure 10:
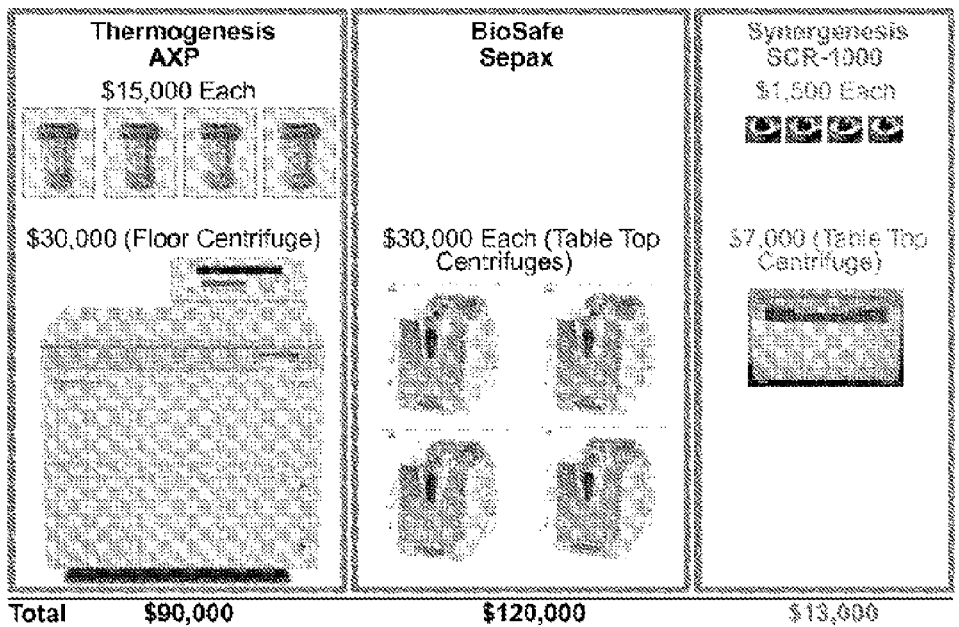
FIG. 10 is a drawing illustrates the relative cost of processing four blood samples with several prior art systems and with the current system.
Figure 12:
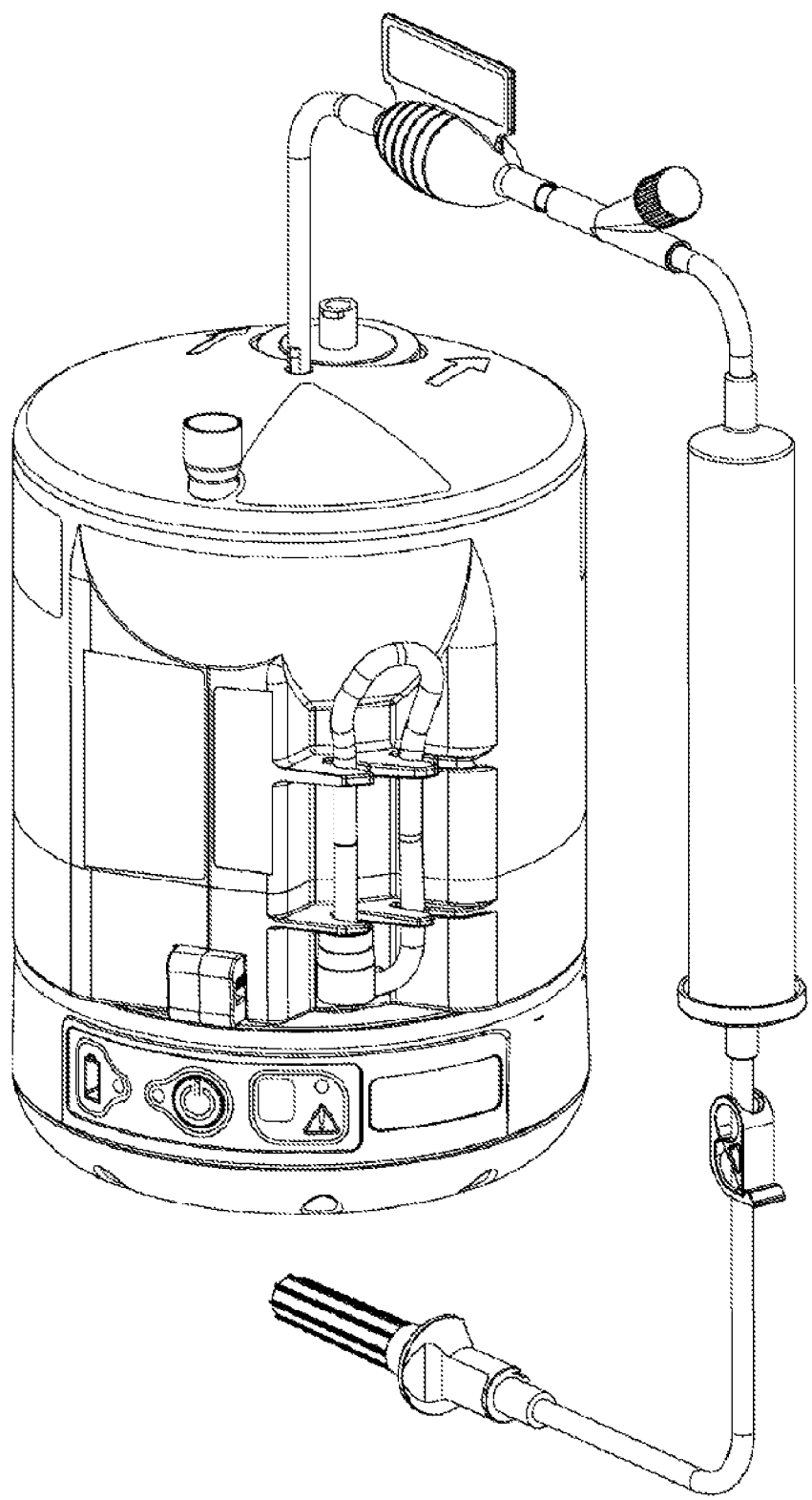
FIG. 12 is a perspective drawing of the disposable cartridge and control module of the present invention.
Figure 13:
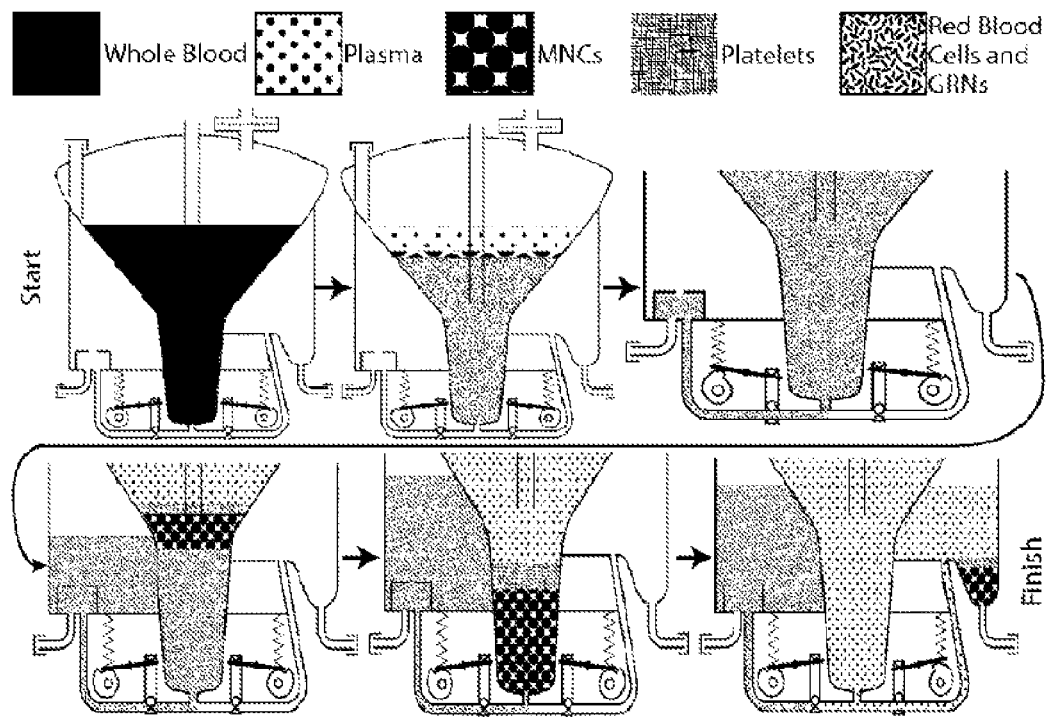
FIG. 13 is a diagram providing an overview of the process of the current invention.
Figure 14:
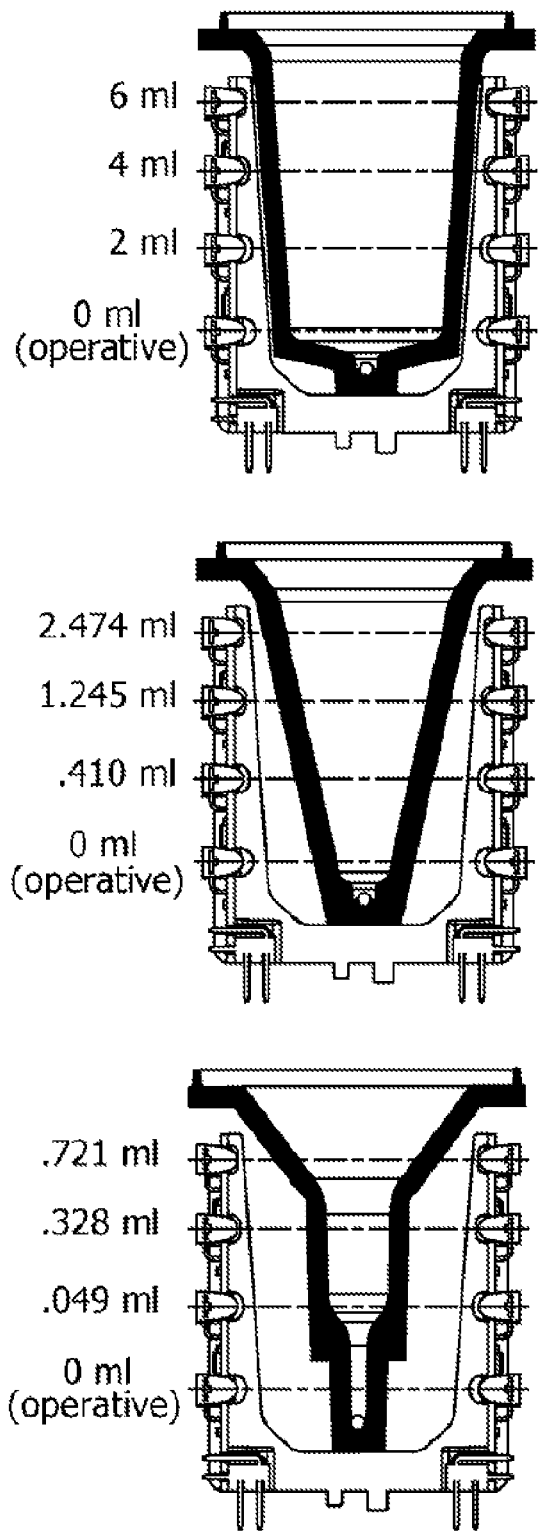
FIG. 14 is a cross-sectional view of several embodiments of the funnel tip of the current invention.
Figure 15:
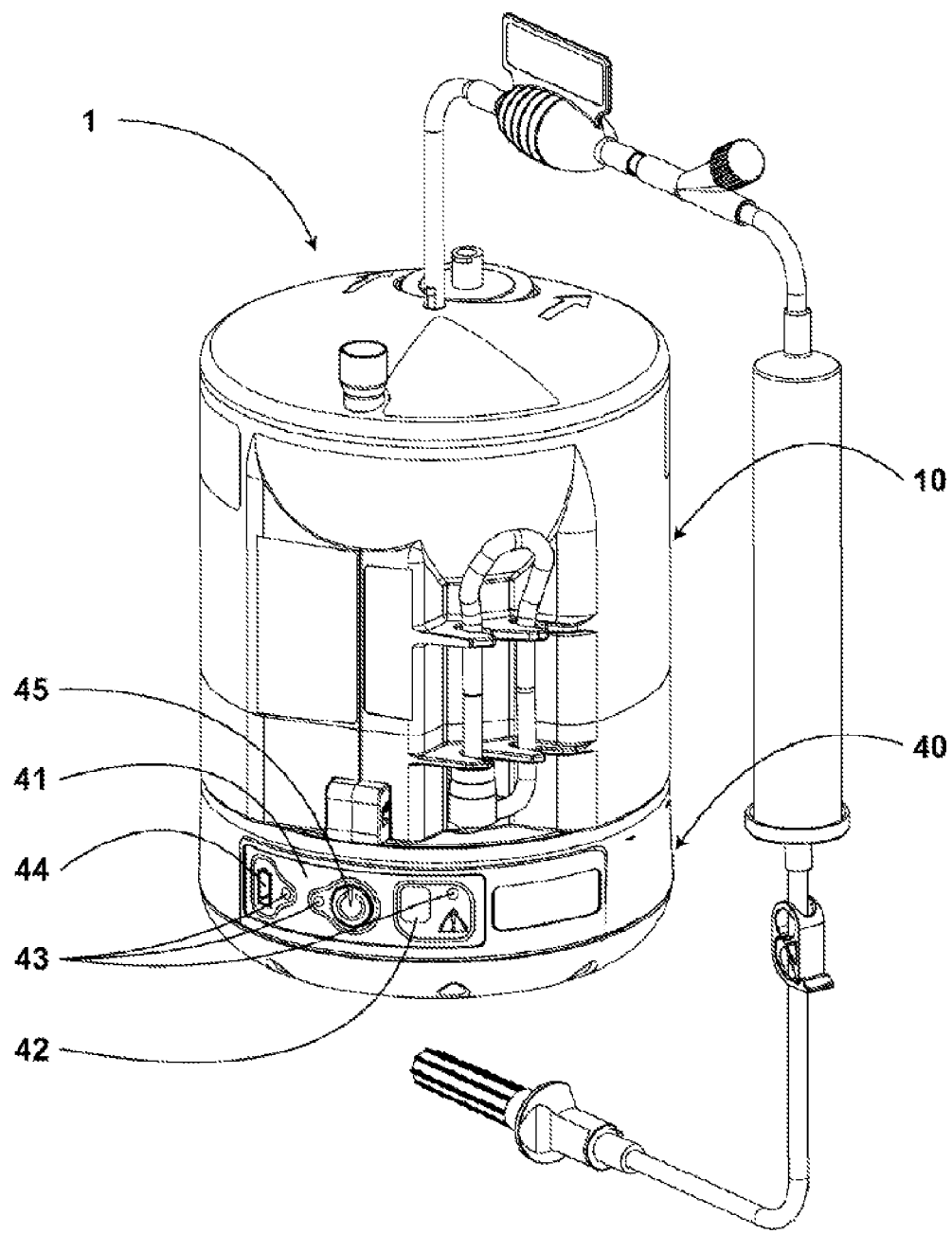
FIG. 15 is a partial wireframe perspective view of the disposable cartridge, control module, and various features of the control module and the cartridge of the present invention.

Turning first to FIG. 15, the applicant's method and device 1 in a preferred embodiment comprises a rigid disposable cartridge 10, which may hold up to 250 mL of liquid, is cylindrical, single-use, and constructed preferably of hard plastic, and more preferably optically clear polycarbonate. The control module 40 in which the disposable cartridge 10 is seated is a battery operated, electro-mechanical device with optical and gravitational sensing. The preferred embodiment also comprises a membrane switch 41, a seven segment digital read out 42 and three light emitting diodes 43 to inform and assist the user. Shown on the left in FIG. 15 is a universal battery sign 44 that alerts the user to the charge condition of the battery. Shown in the center is an on-off switch 45 for the control module and an LED, and on the right is a digital read out 42 and an LED that indicates whether the cell harvest run was performed as designed and, if not, which error in operation may have occurred.

Figure 16:
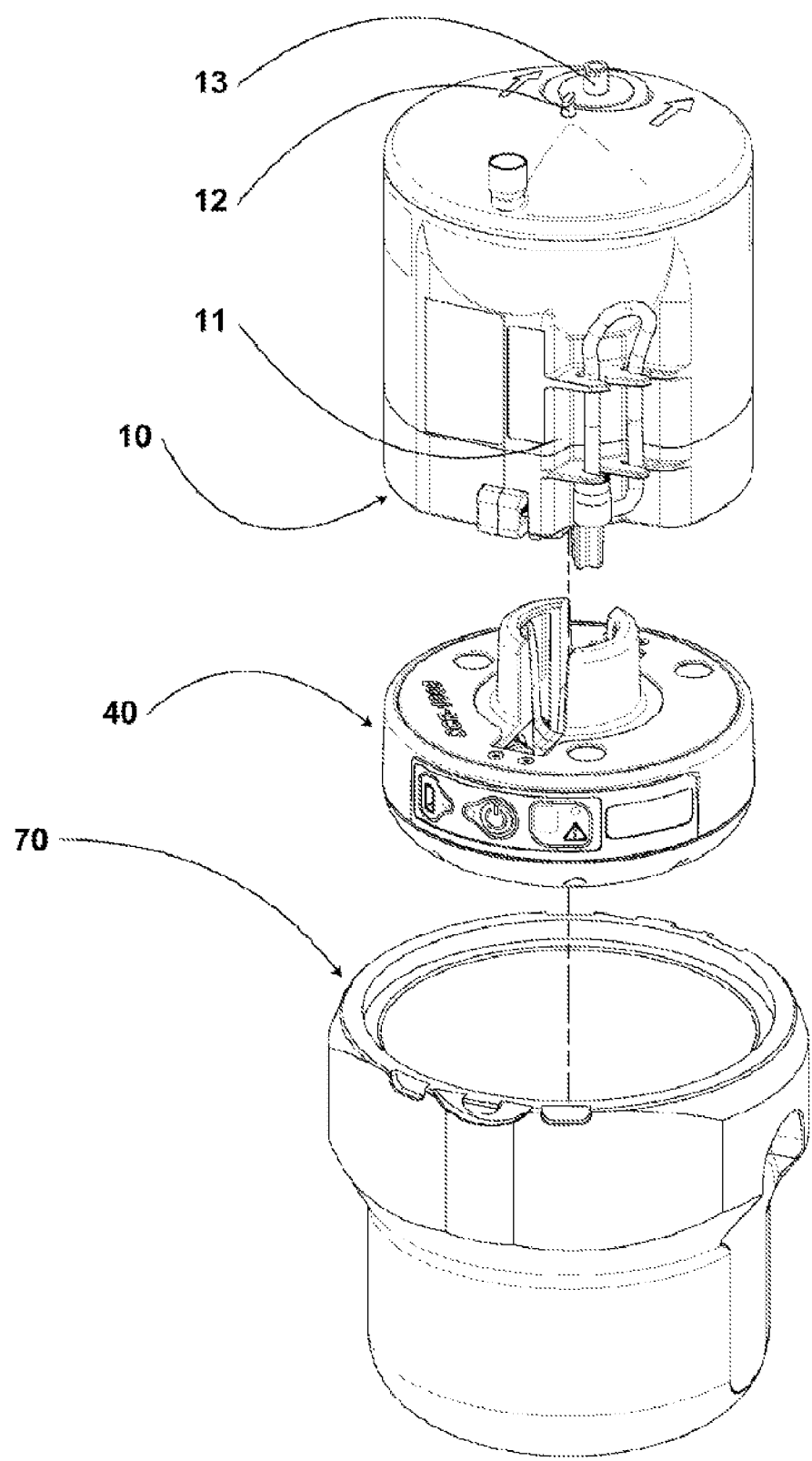
FIG. 16 is an exploded view of the disposable cartridge, control module, and an exemplary centrifuge cup of the present invention.

Turning to FIG. 16, an exploded view of the disposable cartridge 10 and the control module 40, as well as a standard 750 ml centrifuge cup 70 is shown according to the preferred embodiment of the invention. In operation the disposable cartridge 10 and the control module 40 are releasably locked together. The disposable cartridge comprises multiple compartments, one of which is the funnel or rigid chamber 11. Preferably, the centrifuge cup 70 houses the control module 40, which is intended for repeated use with and in connection with the sterile disposable cartridge 10 above it. The control module 40 and cartridge 10, in combination, preferably weigh approximately 450 grams. Among other components to be described later, the cartridge includes an inlet 12 at the top that serves as access for incoming fluid. This access may be connected to tubing which may proceed to a phlebotomy needle or a spike for connecting to a cell solution and may also be coupled to an inline filter that removes any clots that would otherwise jam other system components during the remaining processing steps. The top of the disposable cartridge may also contain a 0.2-micron filter 13 to provide passage for displaced air from within the funnel when blood or bone marrow is introduced into the funnel. The top of the cartridge may also comprise a means of sterile filtering (not shown) of the blood, bone marrow, or other fluids such as diluents, as they are introduced into funnel.

Figure 17:
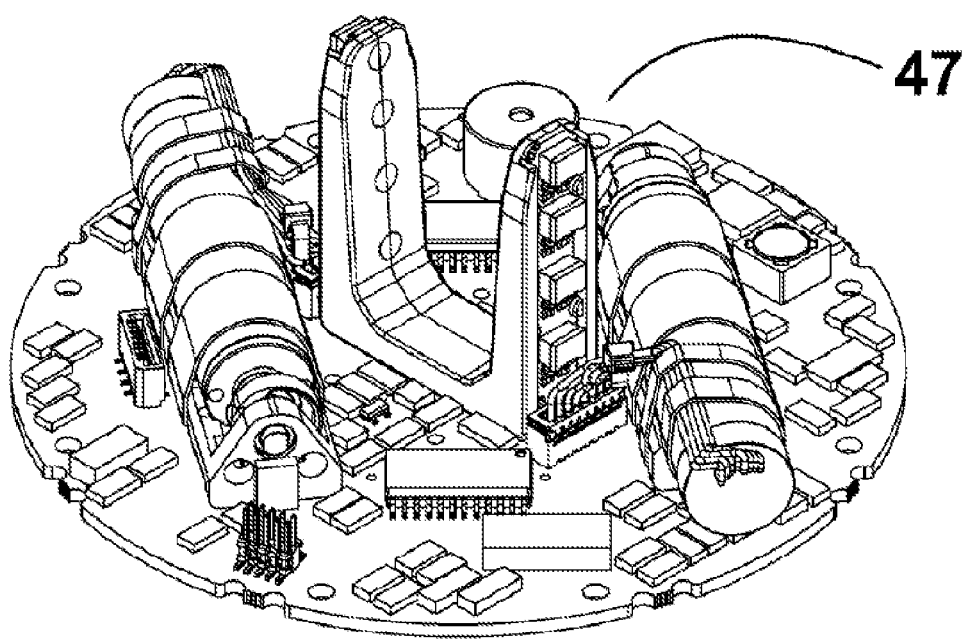
FIG. 17 is a perspective view of the control module of the current invention.

Turning to FIG. 17, the motor circuit board electronics 47, located within the lower control module 40 is shown. The electromechanical portion of the device preferably uses a rechargeable battery system to power a control module that monitors and controls gravitational and optical sensing equipment and directs activity in the disposable cartridge. The means for determining a G force may be any commonly known in the art, such as calculating said force through a measurement of centrifuge RPM, or through direct measurement of acceleration or force.

Figure 18A:
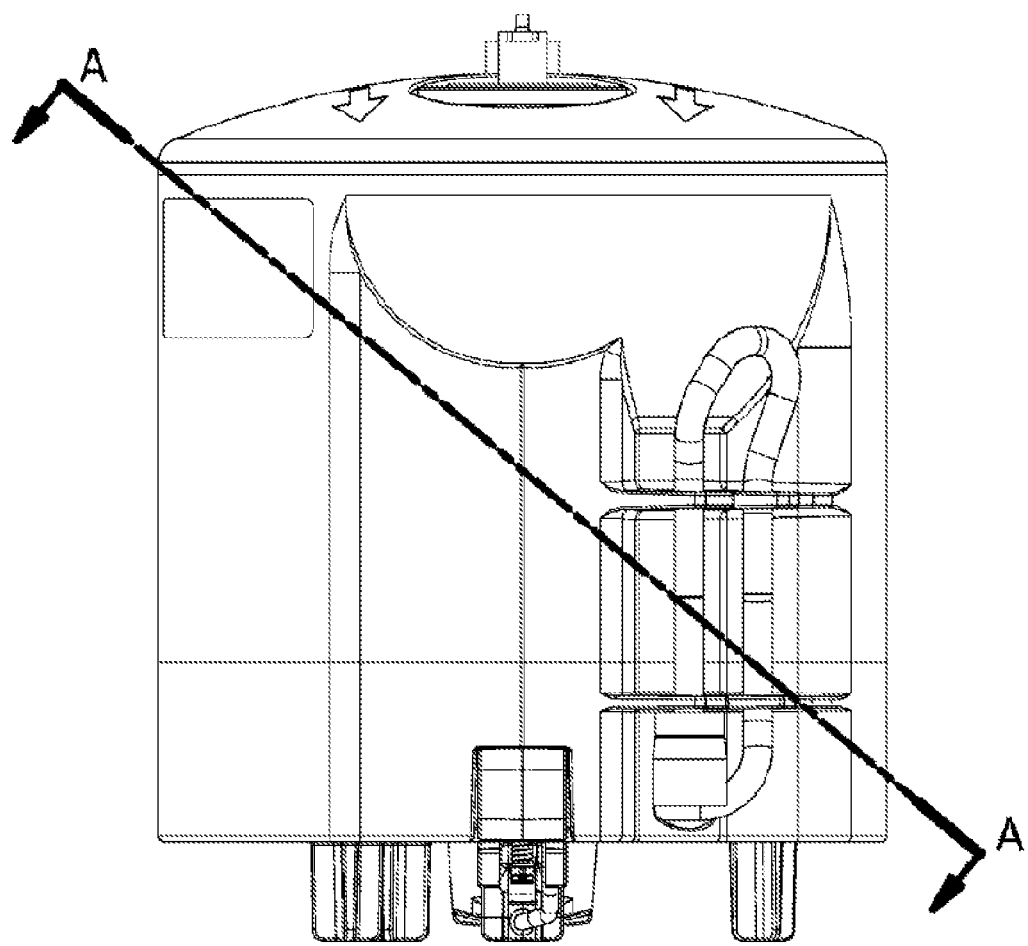
FIG. 18a is a wireframe side view of the disposable cartridge with cut line A-A marked.
Figure 18B:
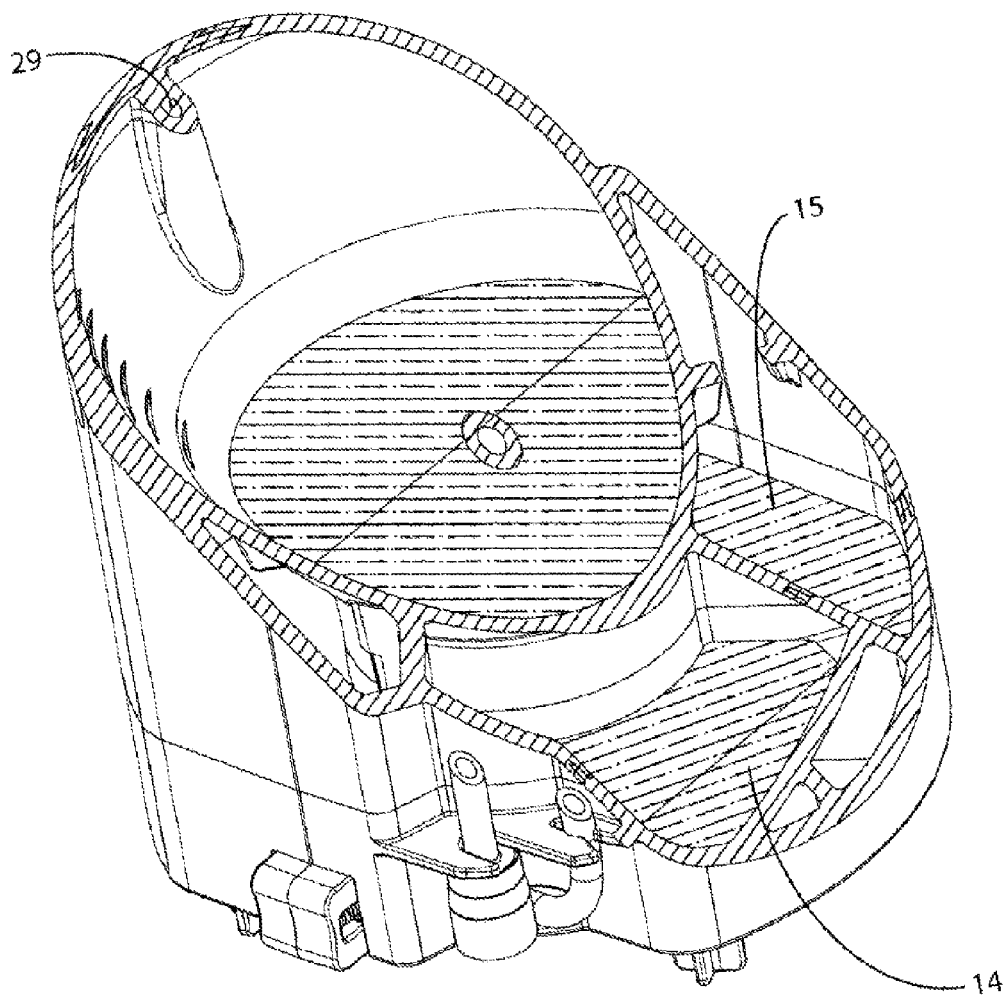
FIG. 18b is a perspective view of the disposable cartridge cut along line A-A.

FIG. 18a shows a diagrammatic side view of the disposable cartridge 10 with labeled cross section A-A. FIG. 18b shows a perspective view of the disposable cartridge 10 cut along cross section A-A. As described in the process below, a biological fluid containing cells, such as normal blood, cord blood or bone marrow, is delivered to the large funnel-shaped compartment having an open end that is initially closed by a valve means (not shown). The cartridge comprises a large first rigid storage compartment or RBC depletion compartment 14 and the smaller second rigid storage compartment or SC compartment 15 into which the WBCs and substantially all the SPCs are transferred. The RBC depletion compartment 14 is significantly larger than the SC harvest compartment 15, as the volume of RBCs depleted from a blood sample is always much greater that the volume of WBCs collected. All compartments are distinct from one another, but contiguous with respect to airflow. The RBC depletion compartment 14 and the SC harvest compartment 15 are connected by small chimneys 29 to the original chamber so as to allow displacement of air as cell solutions move from the original chamber into the compartments.

Figure 19:
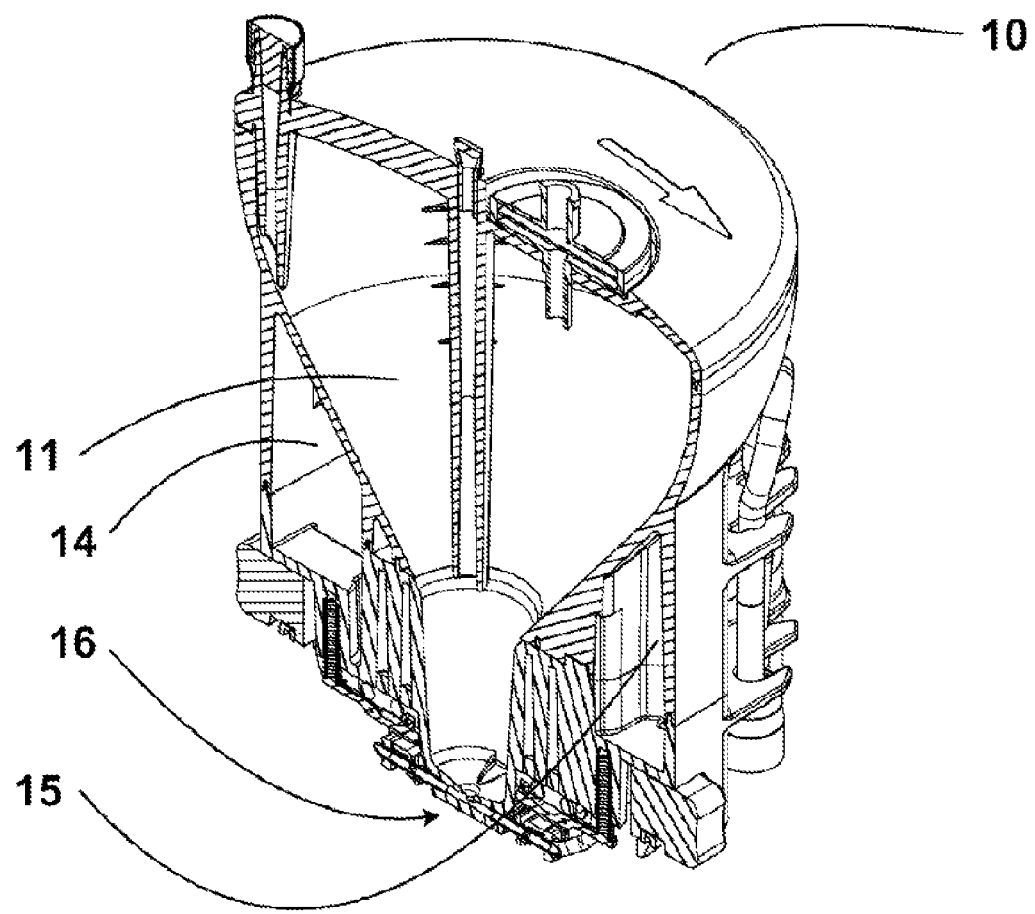
FIG. 19 is a perspective cross-sectional view of a disposable cartridge with the narrow bottom of the funnel shown.

Turning to FIG. 19, a perspective cross-sectional view of a disposable cartridge 10 with a narrow bottom of the funnel 11 is shown. The larger RBC depletion compartment 14 is seen in cross section on the left side of the funnel. As will be described in detail below, in operation, the RBCs initially migrate towards the bottom of the funnel shaped primary compartment, moving radially outward away from the axis of rotation of the centrifuge until reaching the valve system 16 at the bottom of the device. Here, the pressure head of fluid above the valve system urges the fluid into one of two compartments. Which compartment the fluid is directed into is dependent upon the status (open, closed) of valves to those compartments. In either case, after passing through the valve system 16 at the bottom of the cartridge 10, the fluid flows generally toward the axis of rotation, urged by pressure from the of fluid (mostly plasma) remaining in the primary compartment. The fluid that has passed through the valve system is then retained in either the RBC depletion compartment 14 or the SC harvest compartment 15. Through minute adjustments of the valves, unwanted cell solutions may be depleted and desired cell solutions may be harvested.

Figure 20:
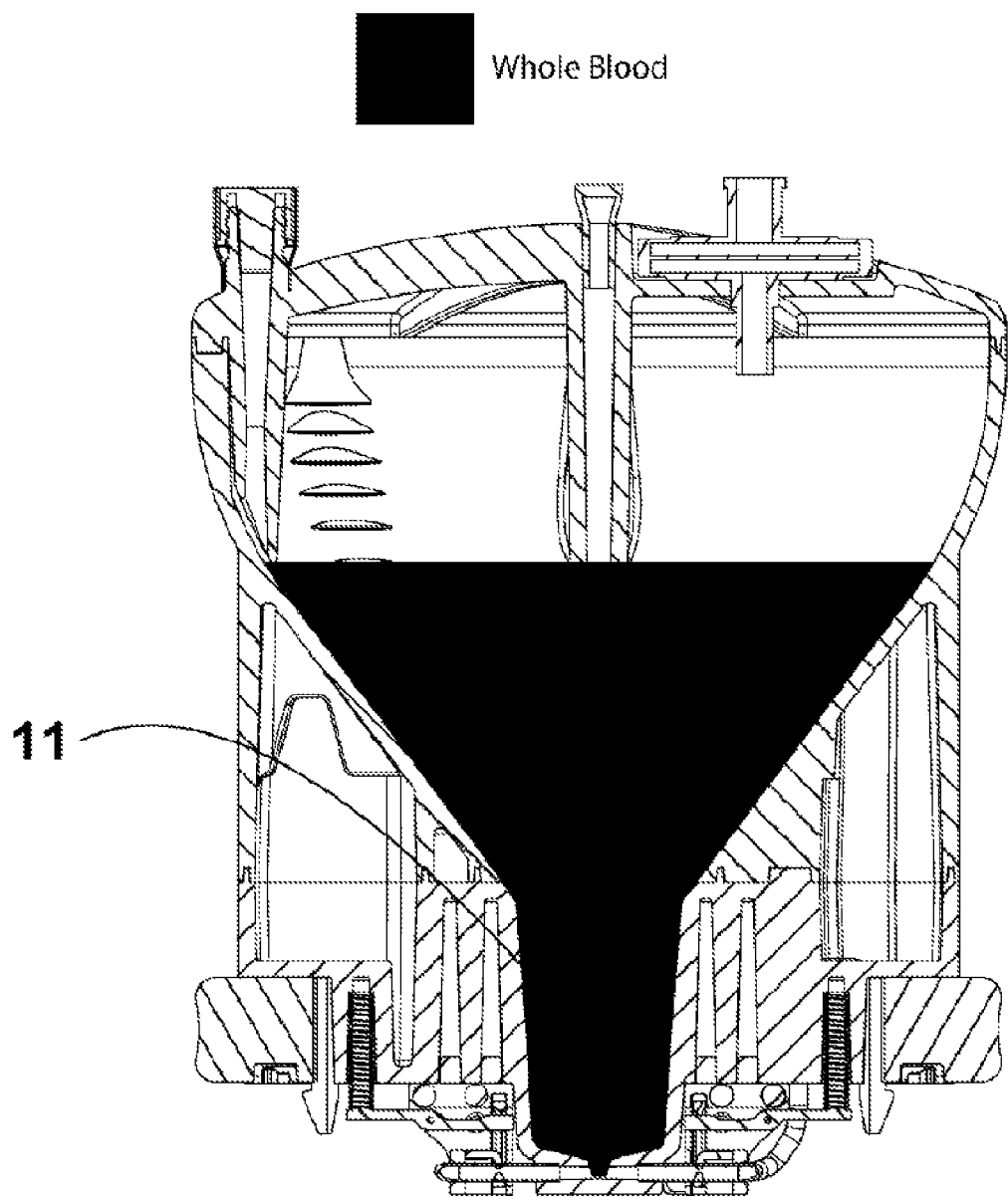
FIG. 20 is a cross-sectional view of a preferred embodiment of the present invention before centrifugation.
Figure 21:
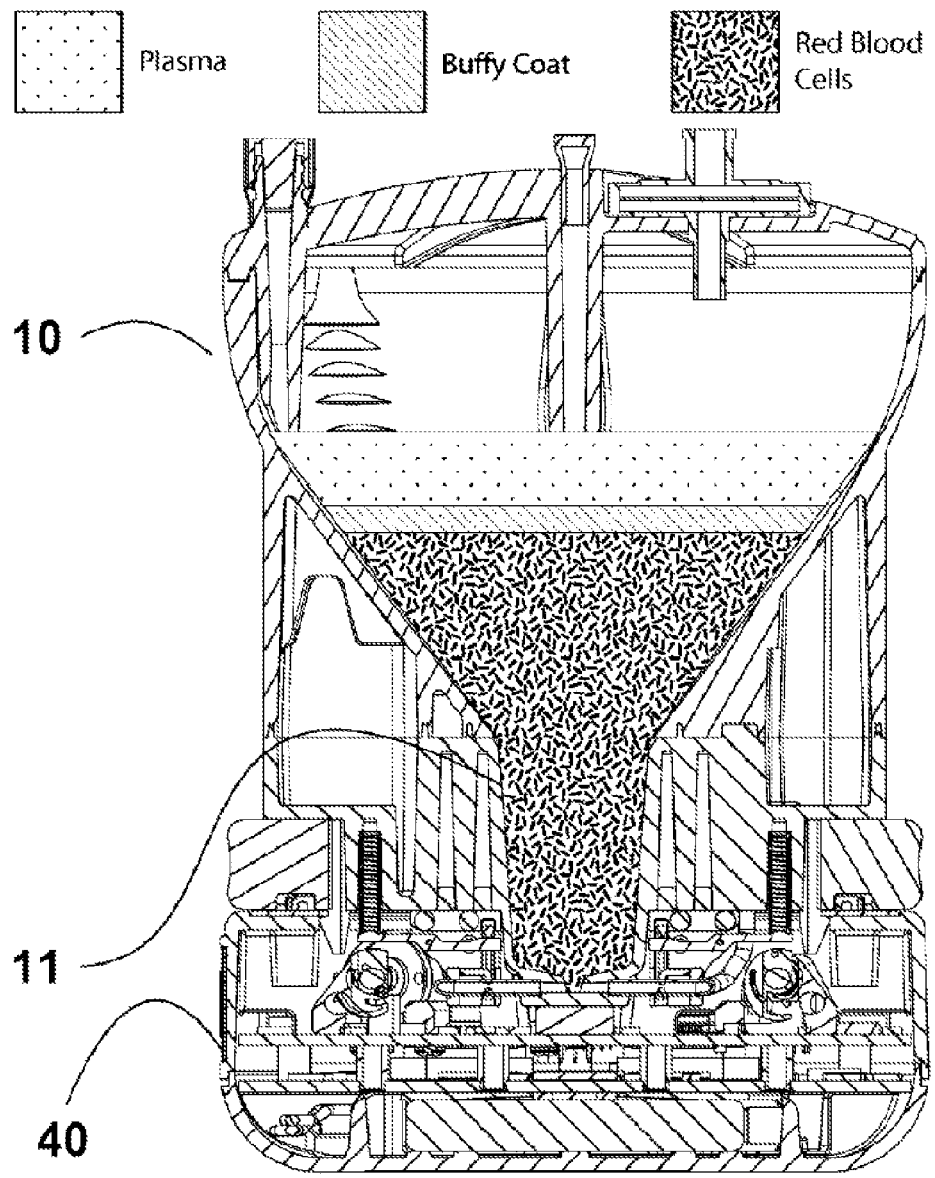
FIG. 21 is a cross-sectional view of a preferred embodiment of the present invention during centrifugation.

Turning to FIG. 20, a preferred embodiment of the present invention is shown in use. As shown, 100 ml of cord blood is placed inside the main funnel shaped compartment 11. The operator then attached the cartridge 10 to the control module 40 (as shown in FIG. 21), and then loads the cartridge into a centrifuge, preferably a swinging bucket centrifuge, such as a Thermo Fisher Sorvall ST-40 tabletop centrifuge configured to accept four 750 ml cylindrical buckets. Alternative centrifuges may be used that provide for more or less than four cartridges to be centrifuged at once.

Turning to FIG. 21, a representation of what occurs when the cartridge 10 is subjected to high G forces is shown. Here, under an exemplary 2000 G centrifugation the RBCs begin to migrate down and the WBCs begin to migrate up from the bottom of the funnel and down from the top volume of the fluid to a position above the RBCs. Above the RBCs then, a very thin layer of WBCs and PLTs begins to stratify and above that a volume of plasma stratifies, the plasma is yellow in color. Under high G forces, the RBCs are increasingly squeezed together near the bottom of the processing funnel 11 with the heaviest of the RBCs lower and the lighter RBCs near the top of the RBC volume. It is noted that because during centrifugation the cartridge depicted in the figure is rotating about an axis perpendicular to and located above the cartridge as shown, the G force experienced by the cartridge increases proportionally to the distance from the axis of rotation and is roughly twice as high at the bottom of the centrifuge cup (2000 Gs) as at the top (1000 Gs).

Figure 22:
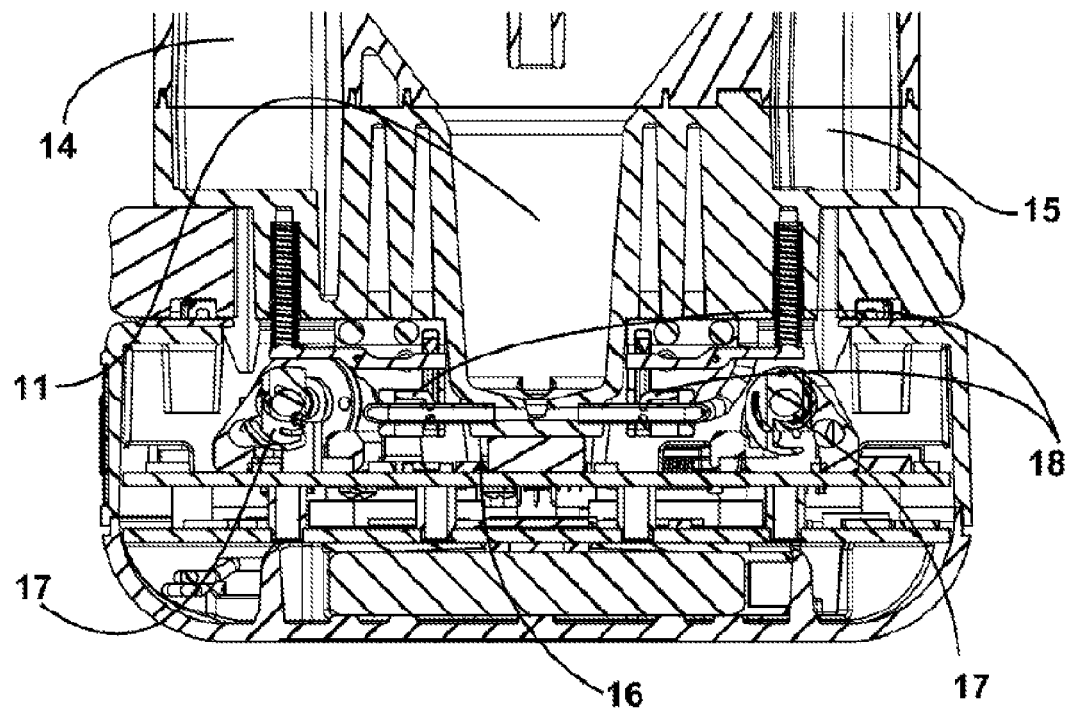
FIG. 22 is a cross-sectional view of the valve system portion of a preferred embodiment of the present invention during centrifugation.

Turning to FIG. 22, a detailed cut away side view of a preferred embodiment is shown. In this preferred embodiment the funnel 11 is kept separated from the RBC depletion compartment 14 and SC harvest compartment 15 by valve system 16. While many means of valve control are contemplated, in a preferred embodiment a pinch valve system is used, wherein eccentric cams 17 control tube pinchers 18 that ultimately direct flow of liquid from the bottom of the funnel to the cell depletion compartment 14 and to the cell harvest compartment 15. Here, the pinch valves comprise two opposing clamps having pinching surfaces approximately 0.088 inches wide, and require approximately 1.6 pounds of pinching force to block all fluid passage through a urethane tube with an inner diameter of 0.062 inches and an exterior diameter of 0.088 inches when the hydraulic pressure in the tube is at 325 PSI. Pinching forces in excess of 1.6 pounds may be required at greater pressures, and reduced pinching forces may be sufficient at lower pressures.

Figure 23:
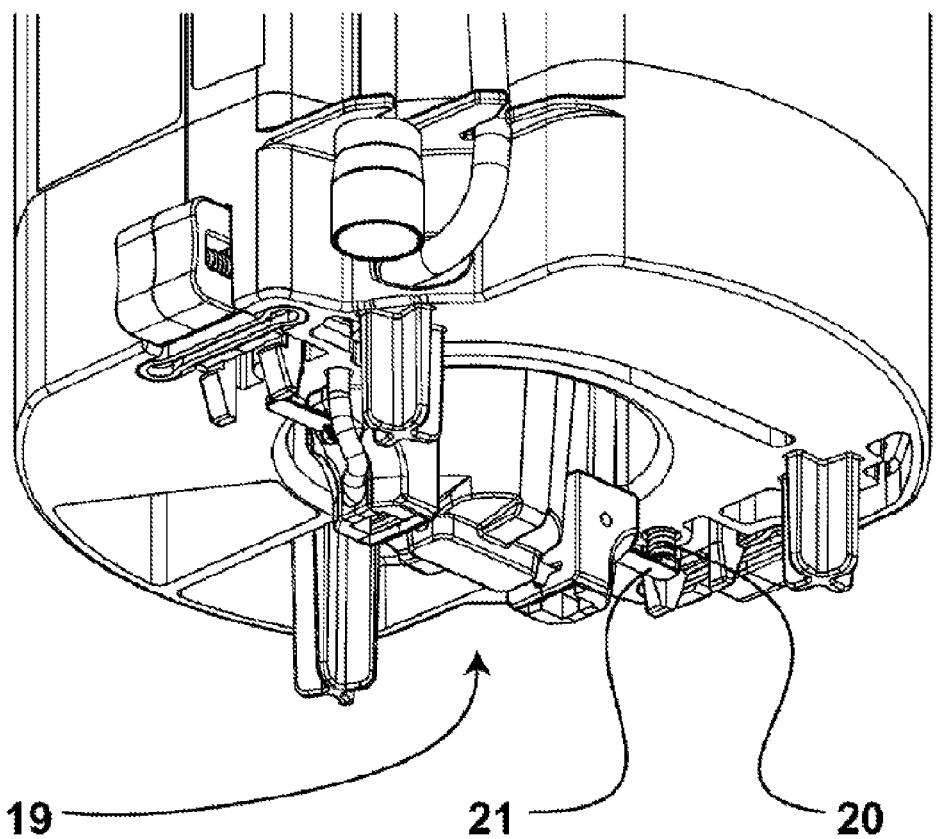
FIG. 23 is a detail view of the cantilever valve system of an alternative embodiment of the current invention.

Turning to FIG. 23, a cantilever system to achieve these required pinching pressures is shown. The cantilever system 19 may open and close the valves (pinch and release the tubing) as needed. The springs 20 for each cantilever 21 are preferably located at the extreme end of the cantilever. The actuator overcomes the resistance of the springs to move the lever. Once the actuator stops applying force, the bias of the springs urges the lever back to its first position.

Figure 24:
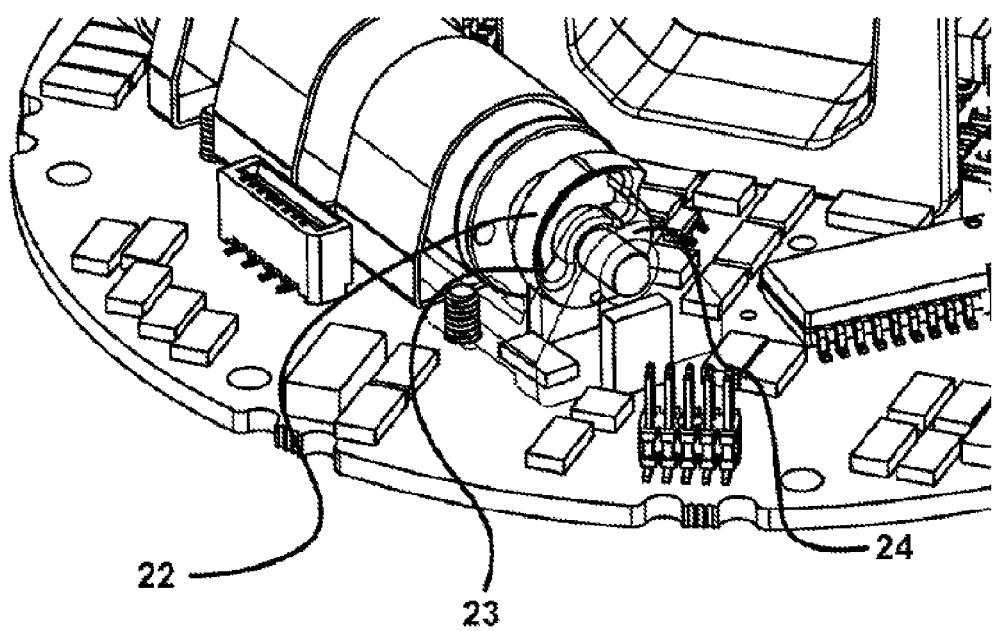
FIG. 24 is a detail perspective view of the cam portion of a preferred embodiment of the present invention.

Turning to FIG. 24, a detailed view of the cam portion of the tube pinching or valve closing mechanism is shown. The cam converts rotational motion of a valve motor into a linear motion, which is used to close or pinch the tube. As disclosed above, a cantilever system may be employed in conjunction with the cam. As the cam 22 rotates approximately 90 degrees clockwise, the larger portion of the cam exerts a continuing clockwise torsional force on the rotor and motor due to the high gravitational field exerting a generally downward force across the entire device. The cam is specially designed to operate within an extremely high gravitational field. The cutout 23 shown and the counterweight 24 located on the opposite side of the cam allow the small motor to provide enough force to rotate the cam counterclockwise 90 degrees to its start position. The cam is thus specifically designed to not only reduce the amount of material off-axis and subjected to potentially immobilizing gravitational forces, but also to counter the weight of the remainder of the cam in light of such forces. That is, as the camshaft rotates about its central axis, this design assures there is no addition or subtraction of torque as a result of G forces acting on the cam.

Figure 25:
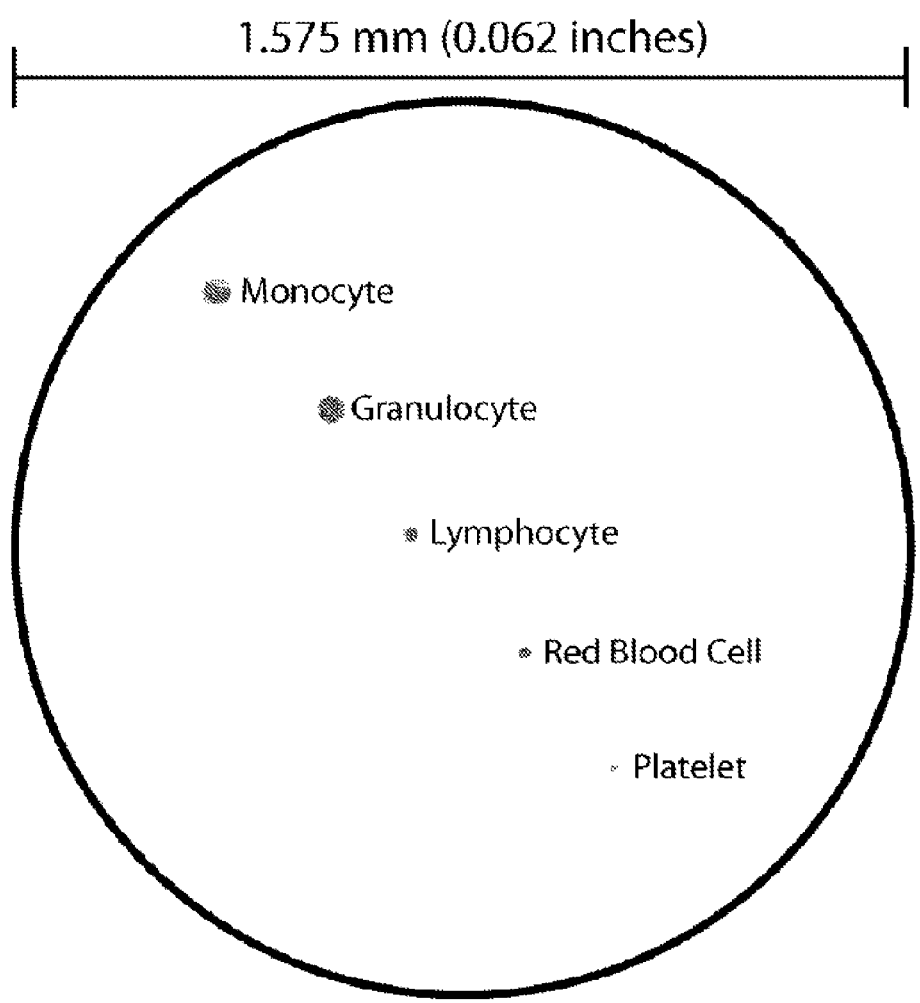
FIG. 25 is a cross-sectional view of the flexible conduit of a preferred embodiment of the present invention, showing the relative size of various cells present in human blood and the flexible conduit.

FIG. 25 shows the relative size of the various cells relative to the connecting tubing or flexible conduit (the large outer circle) of an exemplary embodiment, which is located between the primary compartment 11 and either the RBC depletion compartment 14 or the SC harvest compartment 15. The tubing inner diameter in an exemplary embodiment is 0.062 inch (1.575 mm). Tubing of other inner and outer diameter may be employed, so long as complete cutoff of all cells and liquid is possible via a valve means. In an exemplary embodiment these flexible conduits have a ratio of length to diameter not exceeding 20.

Figure 26:
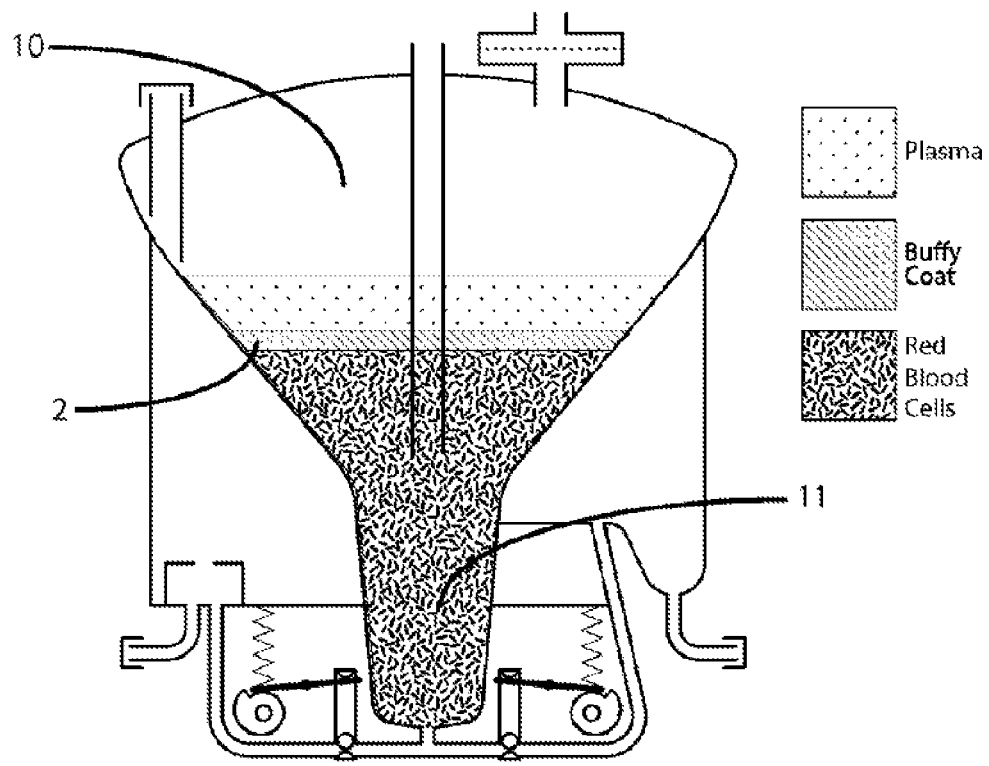
FIG. 26 is a cross-sectional view of a preferred embodiment of the present invention after ten minutes of centrifugation.

Returning to the description of the exemplary process, FIG. 26 shows an exemplary cartridge after approximately 10 minutes of centrifugation at 2000 Gs. The buffy coat 2 stratifies at the interface between RBCs and plasma. The cells at the very bottom of the funnel 11 may reach an HCT (hematocrit, the proportion of blood volume occupied by red blood cells) approaching 90, but towards the top of the RBC layer the HCT may be only 60-70, due to the lower centrifugation force at that distance from the axis of rotation and the wide area of the funnel at that location.

Figure 27:
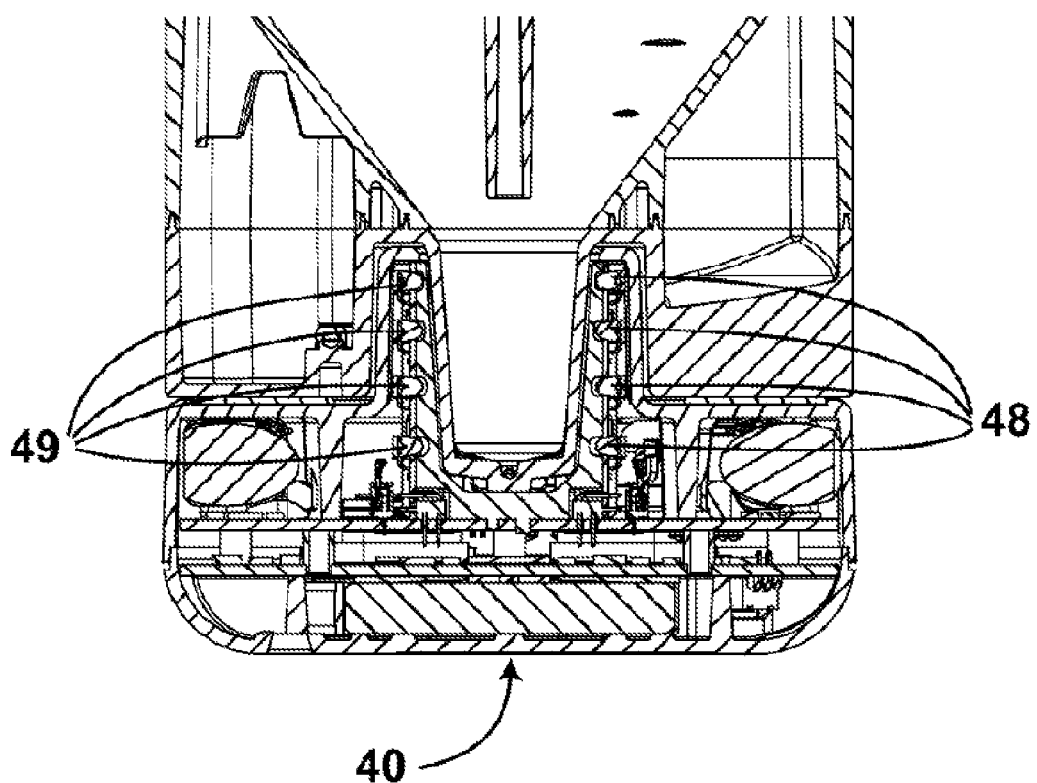
FIG. 27 is a detail cross-sectional view of the optical sensing portion of a preferred embodiment of the present invention.

Turning to FIG. 27, a detailed view of the narrow region of the funnel 11 is shown. When the disposable cartridge 10 is attached to the control module 40, in this narrow region of the primary compartment are at least one but preferably two or more optical or other sensors 48 that detect the type of cells flowing through that portion of the processing funnel. In this narrow region of the primary compartment are also at least one but preferably two or more optical or other emitters 49. In an exemplary embodiment shown four infrared emitters/detector pairs are arranged vertically. In a preferred embodiment infrared sensors are located directly across from paired infrared emitters. In second preferred embodiment, transmitters that provide wavelengths that are preferentially absorbed by red cells are located directly across from paired sensors sensitive to that frequency. In a third preferred embodiment sensors are utilized that identify cells that have absorbed fluorescent dyes. In the first preferred embodiment, the presence of cells interferes with the emitted infrared light and the infrared light detector quantifies the amplitude of the signal penetrating the fluid. In a preferred embodiment the sensors may assign the level of transmission a value from 0-1000. Pure plasma, which similar to water blocks none of the infrared light, will register a value of roughly 1000. As compacted RBCs pass, essentially all infrared light is blocked and the detector registers a value of 0.

Figure 28:
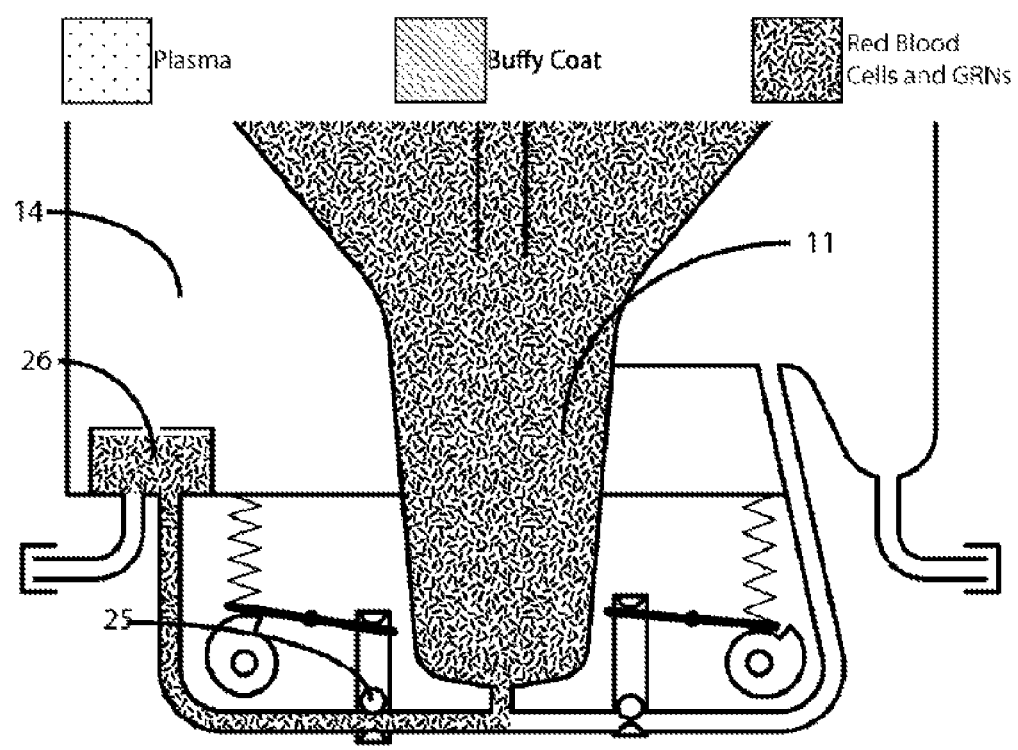
FIG. 28 is a detail cross-sectional view of the valve system, standpipe, RBC collection chamber, and SC collection chamber of a preferred embodiment of the present invention during depletion of RBCs.

Turning to FIG. 28, the next step in the process is shown. After a sample has been centrifuged for a set amount of time (20 minutes in an exemplary embodiment), the centrifuge may slow to a speed that creates 100 Gs at the bottom of the centrifuge bucket (that is, farthest from the axis of rotation). An on-board accelerometer may track the G-force throughout the process. Once the accelerometer detects that the centrifuge has arrived at 100Gs, the device waits a set amount of time (in order to ensure the centrifuge has settled at 100Gs and is not passing through to some lower G-force, such if the machine had malfunctioned or lost partial power), and then a first valve 25 connecting the primary compartment 11 with the RBC depletion compartment 14 opens, allowing passage of highly concentrated RBCs and some plasma. RBCs can be seen entering the depletion compartment 14 by initially filling the standpipe 26 (which preferably has a volume of 1 mL, as will be described below). During use, the RBCs will continue to flow to depletion compartment 14 until the standpipe 26 is full, at which time the RBCs will overflow and fill the larger section of the depletion compartment 14.

Figure 29:
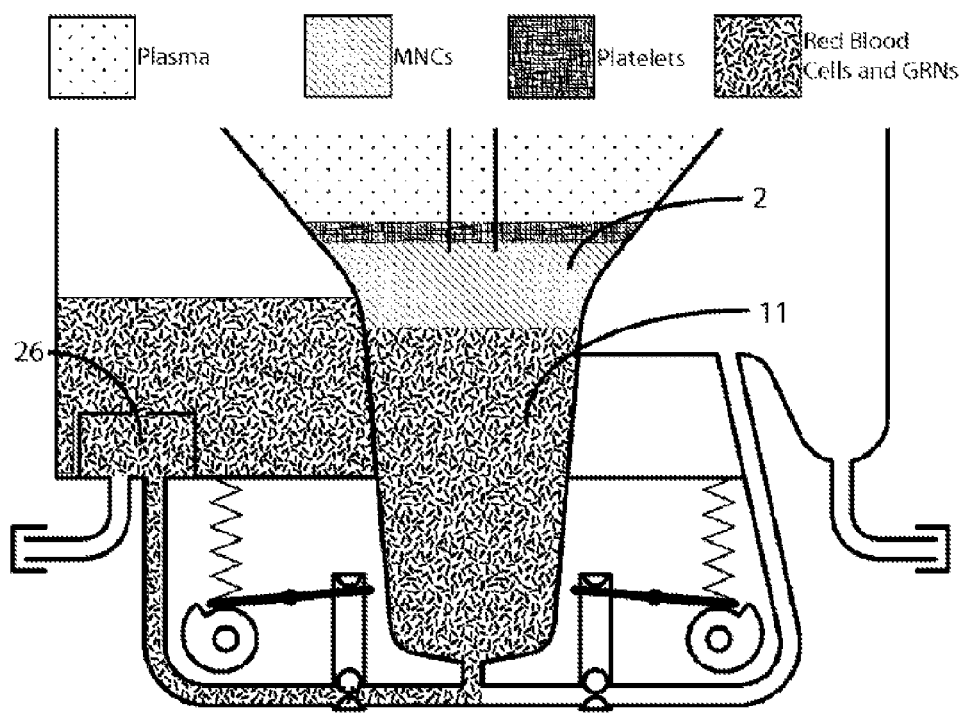
FIG. 29 is a detail cross-sectional view of the valve system, standpipe, RBC collection chamber, and SC collection chamber of a preferred embodiment of the present invention during depletion of RBCs and GRNs.

FIG. 29 shows the standpipe 26 overflowing and the RBCs filling the larger depletion chamber. The interface between RBCs and plasma, delineated by the buffy coat 2, is now readily apparent. As the funnel 11 narrows, the same volume of cells must occupy less horizontal space. As a consequence, the vertical space occupied increases and it becomes easier to distinguish each stratified layer of cell types.

Figure 30:
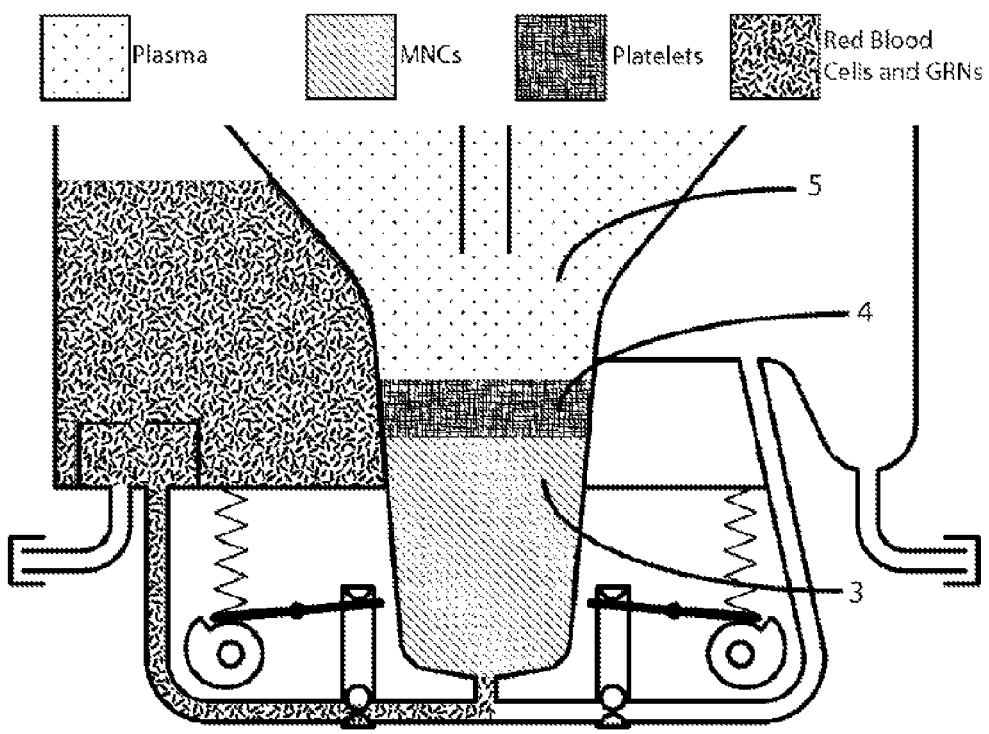
FIG. 30 is a detail cross-sectional view of the valve system, standpipe, RBC collection chamber, and SC collection chamber of a preferred embodiment of the present invention after depletion of RBCs and GRNs.

Turning to FIG. 30, the WBCs entering the narrow portion of the funnel 11 is shown. As the WBCs enter this narrower portion, their stratification continues, with the GRNs on the bottom (not labeled), MNCs 3 in the middle, and PLTs 4 resting on top of the MNCs. The bulk of the plasma 5 in is shown above the PLTs.

Figure 31:
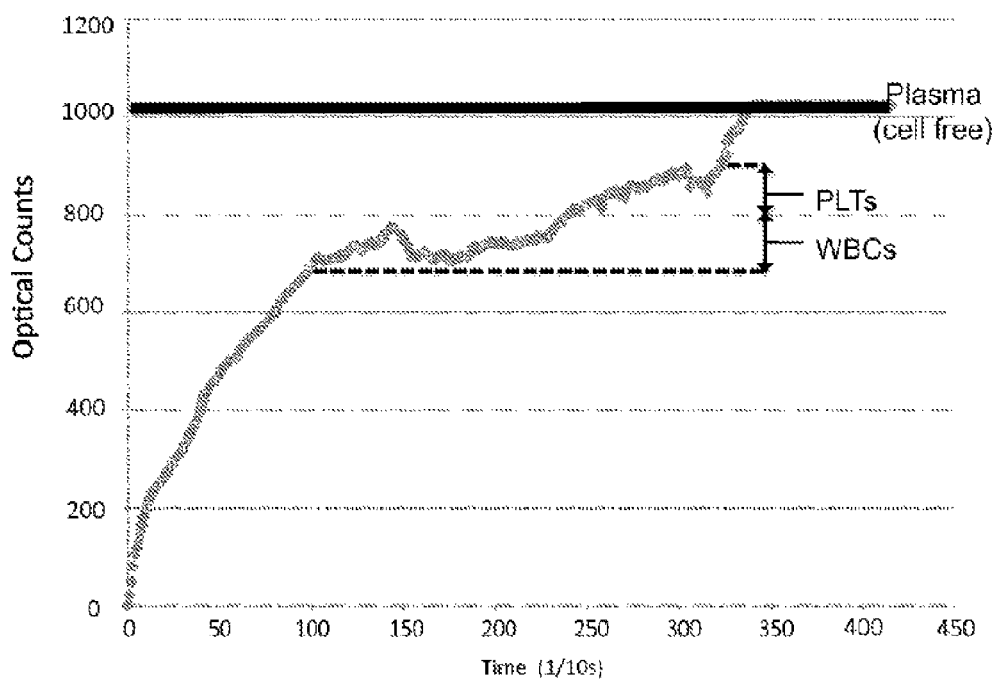
FIG. 31 is a plot of the values measured by a $1^{st}$ position emitter/receive pair of a preferred embodiment of the present invention during depletion of MNCs.

The emitter/detector pairs, as shown in FIG. 27, monitor the passage of the cells through the narrow region of the primary compartment. FIG. 31 shows the infrared optical counts of blood cell populations during the 100 G transit from the $1^{st}$ position (topmost) emitter/detector pair. The horizontal line represents the optical count observed in cell-free plasma. Lower optical counts signify that WBCs and PTLs are still present in the sample being observed by the emitted/detector pair. The initial rise from 0 at the bottom left of the graph indicates when the buffy coat layer disposed above the RBCs passes the $1^{st}$ position emitter/detector pair. The rising value indicates the solution passing between the emitter/detector pairs is becoming clearer, meaning it comprises fewer RBCs. As the clearer layers approach, the value increases, for instance to 50, then 100, 200 and so on.

Under some circumstances the optical count values that are shown in FIG. 31 as rising while cells are depleted, may, when the depletion is halted, begin to fall, indicating that more cells are entering the sensing area. The reasons for this are complex. First, the optical measurements are being taken through a fluid which experiences turbulence and eddies as particles of varying densities are reorganized as they are evacuated through the bottom of a funnel of decreasing radius. RBCs and WBCs fall at differing rates due to their differing sizes. Consequently, if the rate of evacuation of the RBCs is greater than the sedimentation rate for certain particles (such as the PLTs, small in size relative to the others), then those particles will lag behind other particles having faster sedimentation rates. The carefully stratified mixture becomes partially mixed during the evacuation process. Not only do the RBCs fall at one rate while the WBCs fall at a different rate, but also the motion of the WBCs may be inhibited by the motion of the vastly more numerous RBCs. Further, the density of RBCs changes throughout their lifecycle. Consequently, the lighter RBCs will rise with the displaced plasma as the more dense RBCs pack into the bottom of the funnel. Thus the WBCs that began at the bottom of the funnel and which rose towards the RBC/plasma interface are accompanied by the much more numerous "lighter" RBCs. These ascending cells maneuver around the descending dense RBCs due to the fact that all cells possess a slightly negative charge and so tend to repel one another.

To counter this mixing that inevitably occurs during depletion, the an exemplary embodiment of the system, after evacuating for a set time closes the tubing through which the cells are passing and allows the descending cells to re-compact and re-stratify. Upon reopening the tubing, mixing begins to occur again within the funnel. The present invention is thus able to employ a start-stop approach that periodically halts the evacuation process, should this mixing not be suitable for a given application.

Figure 32:
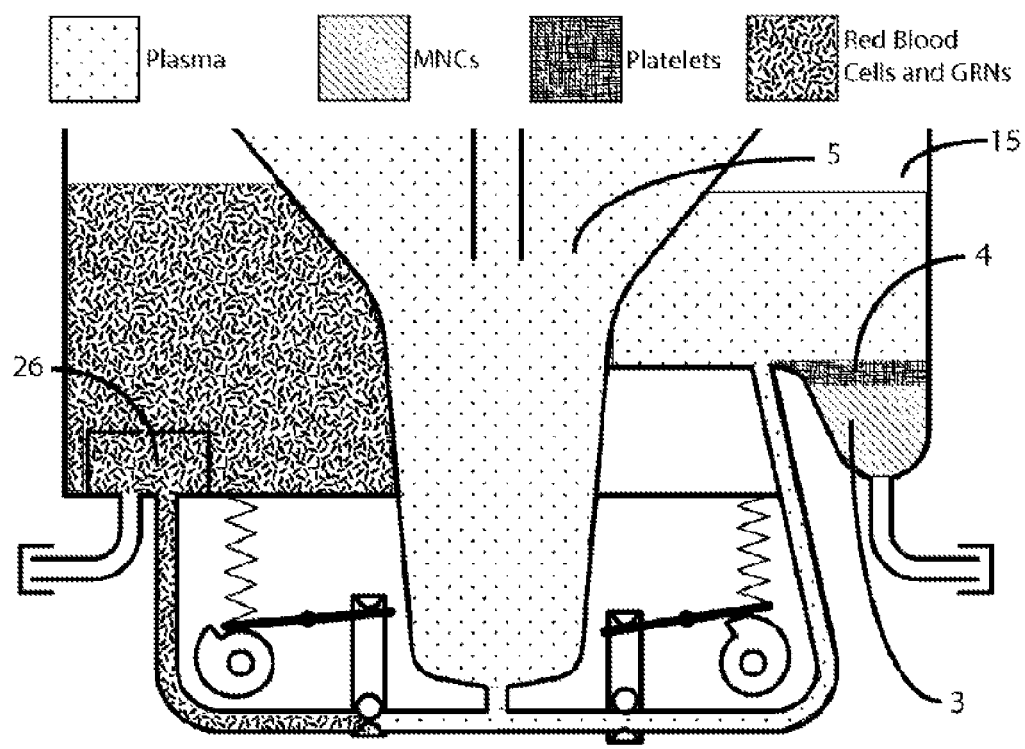
FIG. 32 is a detail cross-sectional view of the valve system, standpipe, RBC collection chamber, and SC collection chamber of a preferred embodiment of the present invention during depletion of MNCs and top-up with plasma.

Turning to FIG. 32, a latter point in the process is shown. At a certain point in the process the tube to the RBC depletion compartment 14 is closed, and the tube to the SC harvesting compartment 15 is opened. FIG. 32 depicts a later time in the process wherein the pathway to the SC harvest compartment 15 has been opened and the pathway to the RBC depletion compartment pinched shut. Because the RBC depletion compartment standpipe 26 holds the final 1 mL of RBCs to enter the RBC depletion compartment 15, the standpipe 26 contains the least dense of the RBCs, and hence a greater concentration of GRNs and NRBCs than does the RBC depletion compartment 15 as a whole. A technician may later recover the contents of the standpipe 26 and thus obtain GRNs and NRBCs for HLA typing without sacrificing the recovery of SPCs from the smaller SC compartment 15. As centrifugation continues, cells of greater density continue to be urged away from the axis of rotation. The plasma 5 remaining in the primary compartment continues to exert pressure on the fluid and cells beneath it, and drives the MNCs 3, and PLTs 4 up the tube leading to the SC harvest compartment 15. As shown, even after the MNCs and PLTs are largely removed from the primary compartment, plasma 5 is allowed to then flow into the SC harvest compartment 15, washing the connecting tube in the process and assuring that all SPCs are collected in the harvest compartment 15.

The timing for controlling the valve system 16 so fluid (and cells) are directed to the SC harvest compartment 15 as opposed to the RBC depletion compartment 14 is critical. If the valves are switched too early, RBCs may enter the SC harvest compartment 15, raising the HCT and decreasing the purity of the sample collected. If the valves are switched too late, some of the MNCs may move to the RBC depletion compartment 14, thereby reducing the recovery of the MNCs and SPCs harvested.

One difficulty present in the prior art that is overcome by an exemplary embodiment of the present invention is the challenge of collecting a predetermined final volume of liquid transferred during centrifugation. This is important for example because various other types of equipment in which it is anticipated blood samples from the current invention will be used are configured to accept a predetermined volume of liquid, such as 20 mL. Although detecting when a certain volume of fluid has been collected during centrifugation is possible with specialized scales measuring the weight of the fluid collected, for reliability purposes a solid-state solution is preferred. To determine the volume of liquid passing through to the SC harvest compartment certain assumptions are required. First, it is known that the fluid above the cells passing through the sensor region of the main compartment is creating downward pressure on those cells and prompting their evacuation through the bottom of the funnel. As the liquid continues to be evacuated under constant acceleration, the rate of evacuation slows because there is less pressure on those cells due to the decreasing volume of plasma above them. It is also known that although cell viscosity may vary from hematocrit to hematocrit and person to person, plasma is adequately consistent with regard to viscosity. Consequently, once all the target cells have passed and only plasma remains to be transferred through the tubing to the SC compartment it will flow at a predictable rate proportionate to the dynamic head of plasma above it.

In the present invention, the above facts are coupled with a method that employs the multiple emitter/detector pairs passed by the evacuated cells. For instance, as the buffy coat approaches the top sensor, the optical count detected by the top, or $1^{st}$ position emitter/detector pair, will begin to rise, as described above. An arbitrary optical count value (in this case 4) is predetermined and a timestamp is initiated when the $1^{st}$ position emitter/detector pair detects that arbitrary value. As evacuation continues, a second timestamp is set when the $2^{nd}$ position emitter/detector pair (that is, the pair just under the topmost pair) reads that same arbitrary value. Through calculations that take into account the distance between the $1^{st}$ position and $2^{nd}$ position emitter/detector pairs, and the time taken for the arbitrary value to reach the $2^{nd}$ position, the velocity of blood component flow between the two pairs of sensors may be determined. The same process may be employed to determine the amount of time it takes any arbitrary value to pass from one sensor to any other sensor located beneath it.

With a further understanding of the volume of blood between sensors, a rate of volume depletion may be calculated. For instance, it is known that in one embodiment of the present invention the volume in the bottom tip of the funnel below the $1^{st}$ position sensor is 6 mL, while the volume below the second position sensor is 4 mL. The rate of flow can thus be calculated based on the understanding that between the first time stamp and the second time stamp, 2 mL of blood is evacuated. The rate may be further refined by detecting when the $3^{rd}$ position and $4^{th}$ position (lowest) emitted/detector pair read that same arbitrary value. Importantly, during this process, the aforementioned start-stop technique is taking place and the effect of full valve closure on the rate of evacuation is noted. In conclusion, through extrapolation based on an observed rate of flow through stacked emitter/detector pairs, a limit can be set on the time that the valve to the SC harvest compartment is open as the solution of WBCs including the SPCs is topped up with plasma to a desired volume. The limit varies dependent on the rate of flow, which ultimately is predominately dependent on the pressure caused by the head of liquid above the evacuation point and, to some extent by the viscosity of the plasma that is used to "top up" the stem cell solution to a predetermined final volume.

In alternative embodiments of the invention RBCs may be collected at higher or lower accelerations then the currently chosen 100 G, for instance in a gravitational field of 50 to 200 Gs.

An alternative embodiment of the invention comprises a method to significantly reduce the number of PLTs 4 which are collected with the MNCs 5.

Figure 33:
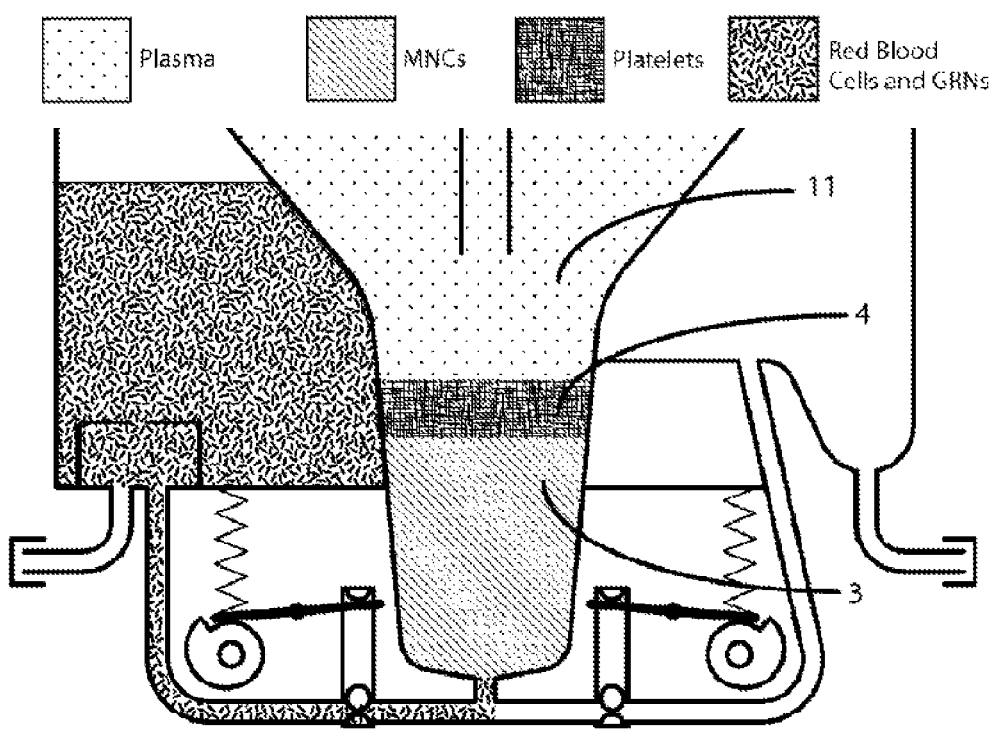
FIG. 33 is a detail cross-sectional view of the funnel, valve system, standpipe, RBC collection chamber, and SC collection chamber of an alternative embodiment wherein centrifugation is stopped after depletion of the RBCs and GRNs.

As is shown in FIG. 33, during the centrifugation process the MNCs 3 and platelets 4 concentrate at the bottom narrow portion of the primary compartment 11. At this point in the process, if the pinch valve to the SC harvest compartment 15 were opened, then the MNCs would be urged by the mass of plasma in a direction first perpendicular to the axis of rotation and then up the right side tube towards the axis of rotation and into the SC harvest compartment 15. Without additional steps taken, the plasma would subsequently force the PLTs into the SC harvest compartment until they were depleted at which time the flow of plasma would top up the SC harvest compartment.

Figure 34:
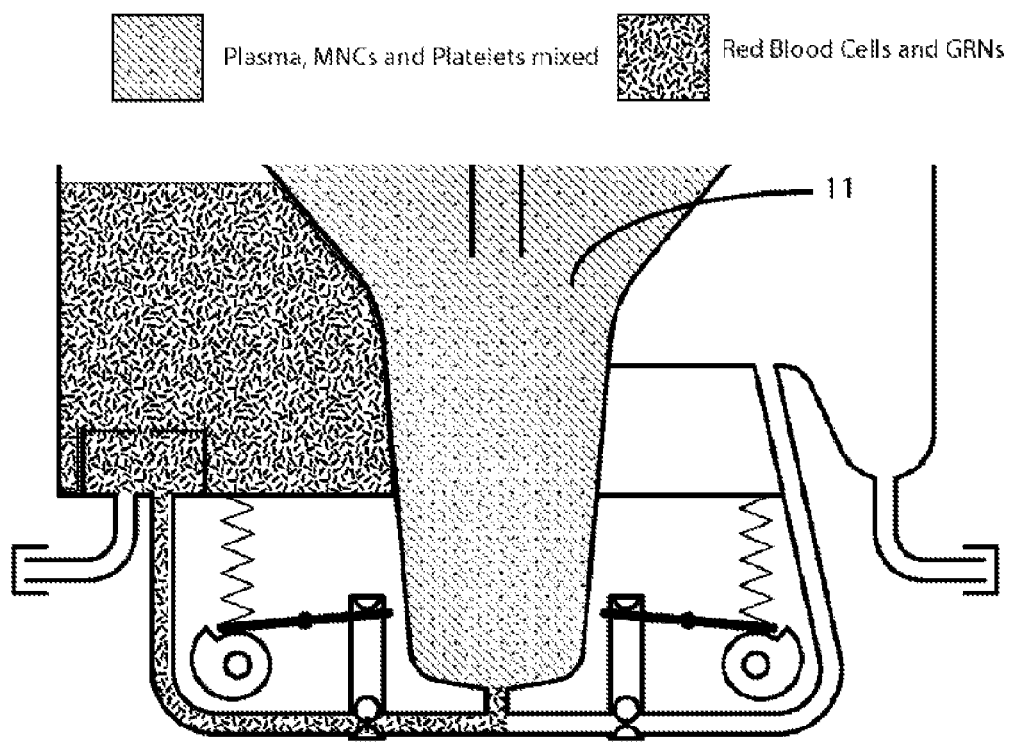
FIG. 34 is a detail cross-sectional view of the funnel, valve system, standpipe, RBC collection chamber, and SC collection chamber of an alternative embodiment wherein centrifugation is stopped after depletion of the RBCs and GRNs and the entire cartridge is shaken so as to mix the remaining plasma, MNCs, and PLTs.

To reduce the number of PLTs that enter the SC harvest compartment 15, the technician may program the control module to pause the harvest process at the end of the RBC/GRN depletion cycle (by closing the RBC valve and not opening the MNC valve) and allow the centrifuge to come to a stop. In this method, the technician then removes the cartridge from the centrifuge bucket and gently rocks the cartridge in order to redistribute MNCs 3 and PLTs 4 throughout the plasma 5 in the funnel, dispersing them as depicted in FIG. 34.

Figure 35:
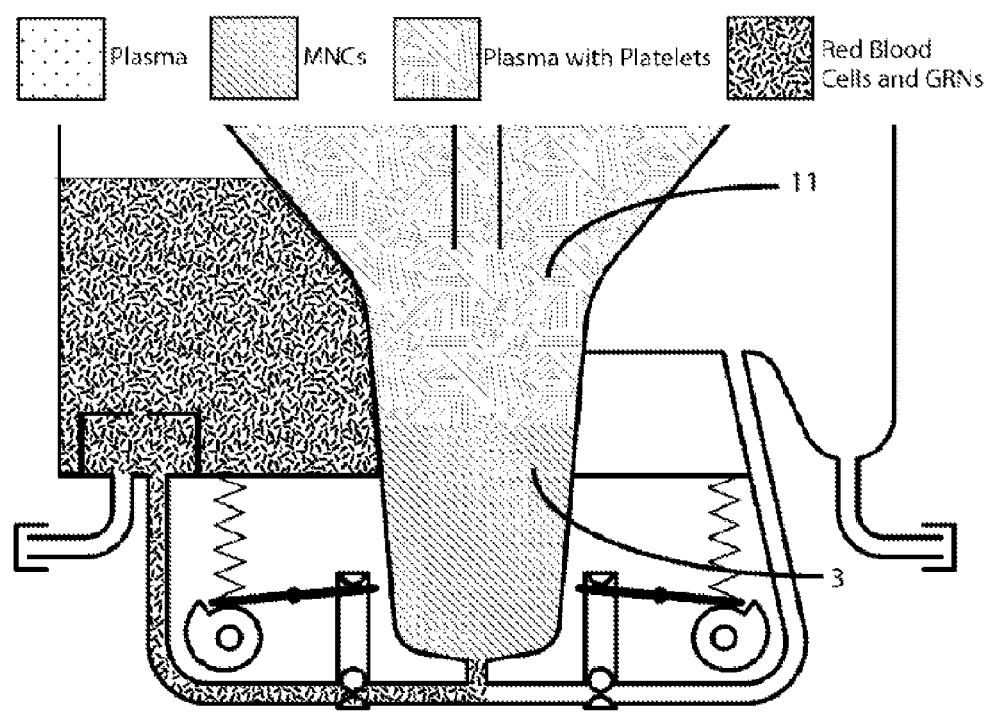
FIG. 35 is a detail cross-sectional view of the funnel, valve system, standpipe, RBC collection chamber, and SC collection chamber of an alternative embodiment wherein the cartridge is centrifuged a second time at lower G force and for less time so as to collect substantially all the MNCs but only a small portion of the PLTs.

As shown in FIG. 35, the cartridge is then centrifuged for a smaller amount of time and at a lower acceleration. The smaller amount of time and lower acceleration is sufficient to cause the denser and faster moving MNCs 3 to reconcentrate at the bottom of the funnel, but not enough to cause the PLTs to do the same. The PLTs are of lower density and size, and thus require more time to migrate to the bottom of the funnel. By not providing that time, the majority of the MNCs can be separated from the majority of the PLTs as shown.

Figure 36:
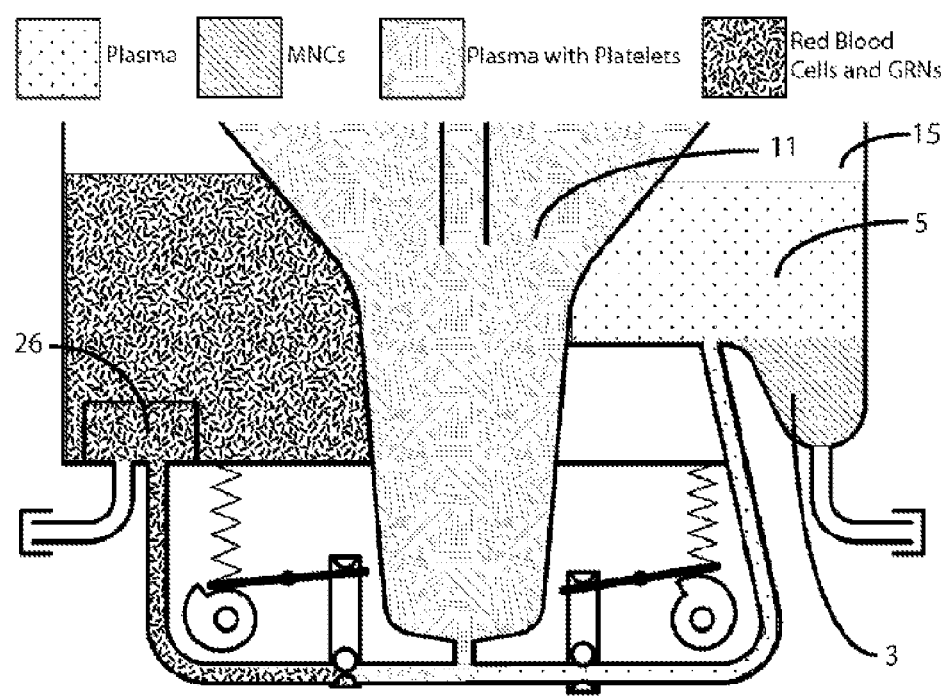
FIG. 36 is a detail cross-sectional view of the funnel, valve system, standpipe, RBC collection chamber, and SC collection chamber of an alternative embodiment after centrifugation is stopped and MNCs, plasma, and a small portion of PLTs are collected in the SC harvest compartment.

Turning to FIG. 36, when the pinch valve to the SC harvest compartment 15 is then opened, the MNCs 3 flow first, followed by plasma 5 and a small fraction of PLTs 4 and then the SC harvest tubing is pinched closed. While some PLTs still make it into the SC harvest compartment, the fraction is proportional to the volume of plasma that was transferred into the SC harvest compartment compared to the total volume of plasma in the disposable cartridge. For example a 100 ml volume of blood would typically contain about 55 ml of plasma. If 5 ml of plasma were transferred to the SC harvest compartment, leaving 50 ml of plasma behind in the primary compartment, then the proportion of PLTs with the MNCs would be about 10% of the total PLTs—constituting a roughly 90% reduction of PLTs in the MNC harvest.

Figure 37:
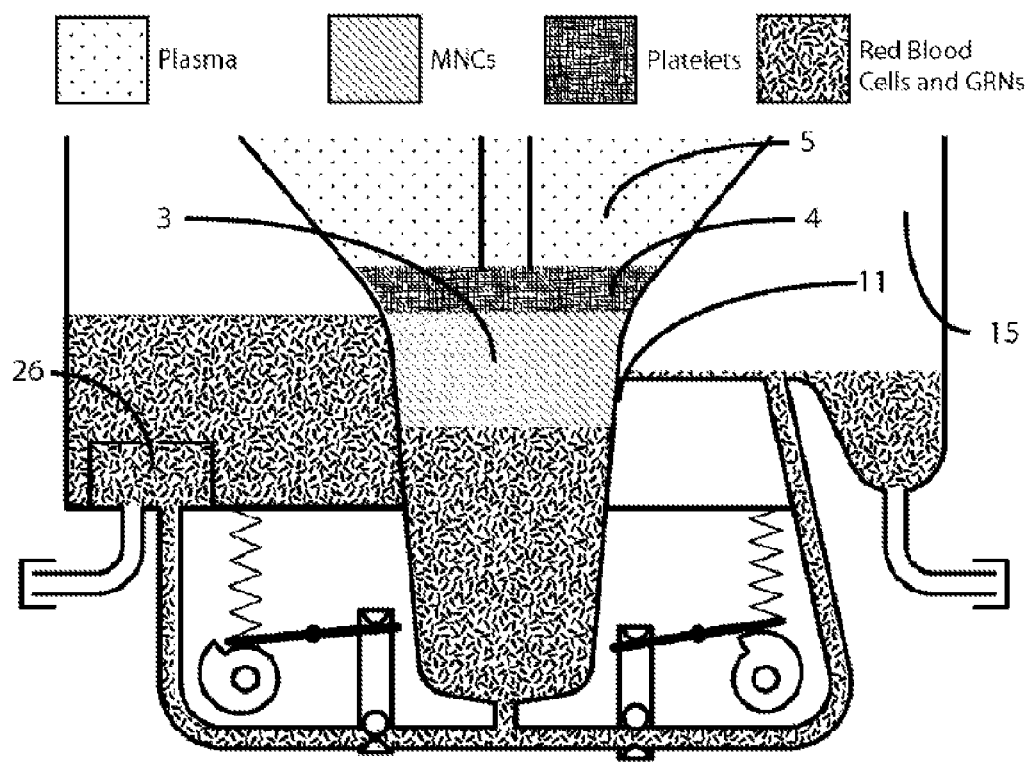
FIG. 37 is a detail cross-sectional view of the funnel, valve system, standpipe, RBC collection chamber, and SC collection chamber of an alternative embodiment in which GRNs are desired in the SC harvest compartment.

Turning to FIG. 37, another alternative embodiment is illustrated. In this alternative embodiment of the invention, GRNs 6 may be desired in the SC harvest compartment 15. For instance, in the collection of cord blood, the total WBC count often determines which of two cord blood units equally matched to the patient is chosen. Therefore it may be desired to include the majority of GRNs with the MNCs. To obtain this result, the technician may program the control module to open the valve to the SC harvest compartment earlier than in the other (above disclosed) embodiments, thereby allowing the top layer of RBCs (comprising many of the GRNs) into the harvest compartment. It should be readily apparent that through adjustments in timing, varying amounts of GRNs may be allowed into the SC harvest compartment. The sample collected in the harvest compartment is subsequently topped off with plasma so that the sample retains a relatively low (approximately 2-10% hematocrit).

Figure 38:
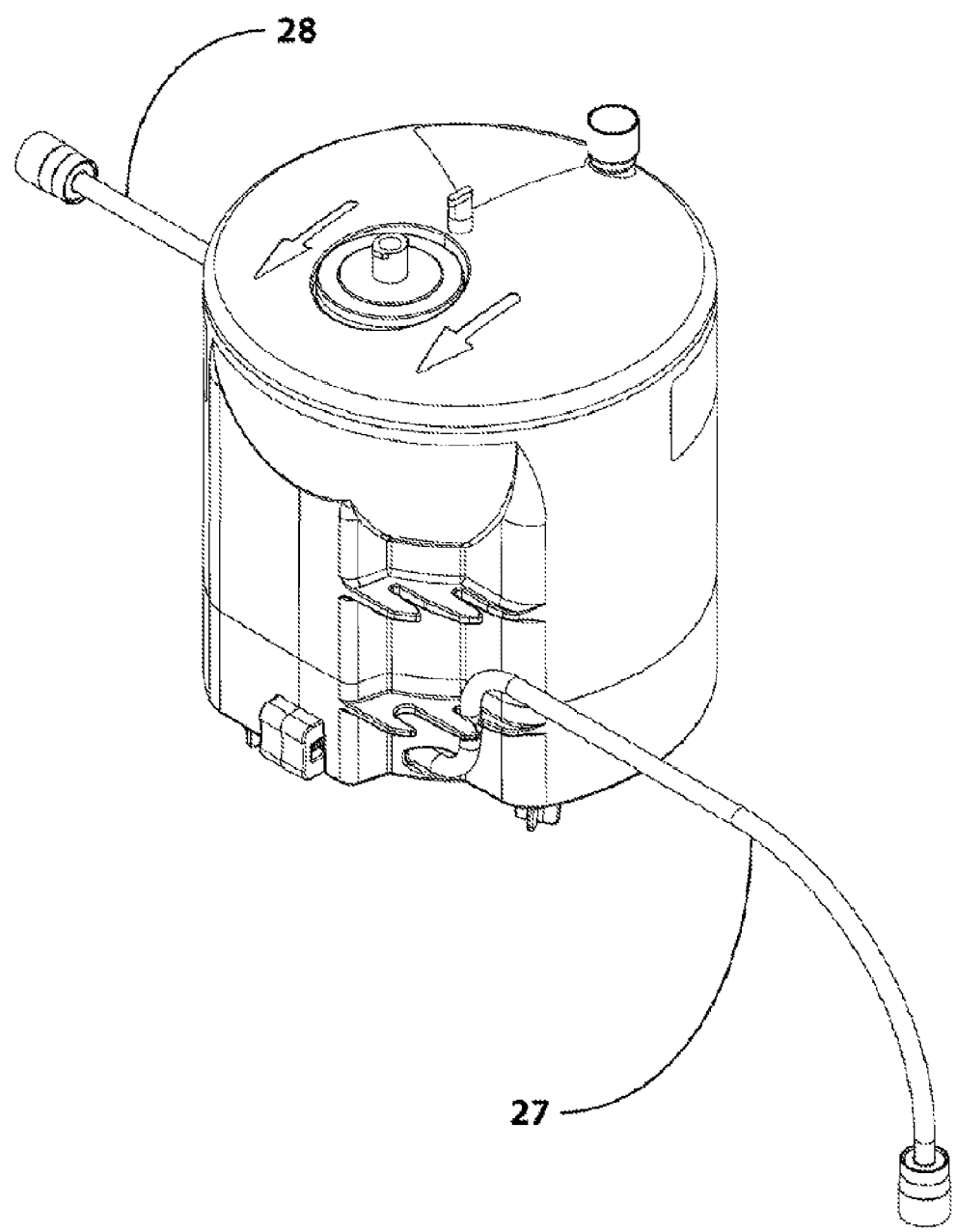
FIG. 38 is a perspective view of the cartridge of a preferred embodiment of the current invention showing the SC harvest tube and the RBC/GRN harvest tube.

Turning to FIG. 38, in any of the above embodiments, mechanisms are in place for removing the contents of the SC harvest compartment as well as the standpipe which contains the last 1 mL of RBCs transferred to the RBC compartment. FIG. 38 shows the disposable cartridge with both the SC harvest tube 27 and the RBC/GRN harvest tube 28 deployed for collection. The RBC/GRN harvest tube connects to the exterior of the cartridge by any means known in the art, and creates a fluid connection with the bottom of the standpipe, thereby providing a simple means to retrieve NRBCs and GRNs from the last 1 mL of the cell solution for sampling, such as obtaining human leukocyte antigen (HLA) typing, and then the remainder of the RBC/GRNs can also be removed, as required.

In any embodiment of the present invention, it is to be understood that antibody beads, either bouyant in plasma or approximately as dense as RBCs, may be introduced to the sample prior to harvesting to bind to cells known to not be useful for a specific research or clinical purpose.

In any embodiment of the present invention, it should be readily understood that fluorescent material absorbable by certain cell populations may be introduced to the sample prior to harvesting to allow tracking of said cell populations through the harvesting process and thereafter.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

The invention claimed is:

1. A method for depleting at least one of red blood cells, granulocytes, or platelets from a sample comprising blood, bone marrow, or stromal vascular fraction cells separated from adipose tissue, the method comprising:
   a. placing a rigid cartridge within a centrifuge, said rigid cartridge comprising a rigid chamber having an end that is fluidly connected to a valve system comprising at least one valve which is initially closed, a first rigid storage compartment, and a second rigid storage compartment;
   b. transferring said sample into said rigid chamber, said sample comprising platelets, plasma, cells of high density, and cells of low density;
   c. centrifuging said rigid cartridge such that said sample is urged toward said end by a first G force of at least 10 G and then by a second G force lower than said first G force;

d. providing a first pathway for said cells of high density through said end and to said first rigid storage compartment;
e. tracking a migration of said cells of high density through said end; and
f. providing a second pathway for said cells of low density and an amount of platelets and plasma through said end and to said second rigid storage compartment.

2. The method according to claim 1 wherein said tracking is done optically.

3. The method according to claim 1 wherein both said providing steps utilizes said valve system.

4. The method according to claim 1 wherein said rigid chamber is generally conical.

5. The method according to claim 1 further comprising detecting said first and second G force.

6. The method according to claim 1 further comprising depleting at least one additional cell type from said sample.

7. The method according to claim 6 further comprising the steps of:
  a. decelerating said rigid cartridge to a G force of 1 G subsequent to said centrifuging step and wherein a portion of said sample remains in said rigid chamber;
  b. agitating said rigid cartridge to mix said portion; and
  c. centrifuging said rigid cartridge to a G force greater than 1 G for subsequent processing.

8. The method according to claim 1 wherein a plurality of flexible conduits connect said rigid chamber to said first and said second rigid storage compartments, and wherein said flexible conduits have a ratio of length to diameter not exceeding 20.

9. The method according to claim 1 wherein the valve system comprises a cam and flexible conduit.

10. The method according to claim 1 wherein an antibody bead is introduced to said sample prior to said providing step.

11. The method according to claim 10 wherein said antibody bead is buoyant in plasma.

12. The method according to claim 1 wherein said sample further comprises a fluorescent material.

13. The method according to claim 12 further comprising the step of tracking said fluorescent material.

14. The method according to claim 1 further comprising the steps of:
  a. decelerating said rigid cartridge to a G force of 1 G subsequent to said centrifuging step and wherein a portion of said sample remains in said rigid chamber;
  b. agitating said rigid cartridge to mix said portion; and
  c. centrifuging said rigid cartridge to a G force greater than 1 G for subsequent processing.

15. The method according to claim 14 wherein an antibody bead is introduced to said sample prior to said providing step.

16. The method according to claim 15 wherein said antibody bead is buoyant in plasma.

17. The method according to claim 14 wherein said sample further comprises a fluorescent material.

18. The method according to claim 17 further comprising the step of tracking said fluorescent material.

19. The method according to claim 1 further comprising the step of adding a red blood cell sedimentation acceleration agent.

20. A method for depleting at least one of red blood cells, granulocytes, or platelets from a sample comprising blood, bone marrow, or stromal vascular fraction cells separated from adipose tissue, the method comprising:
  a. providing:
    i. a centrifuge having an axis of rotation;
    ii. said sample comprising plasma and a first portion of high density and a remaining portion of low density;
    iii. a rigid cartridge comprising:
      1. an internal rigid chamber having an exit port;
      2. a first rigid storage compartment and a second rigid storage compartment;
      3. an input port; and
      4. a valve system comprising at least one valve and providing communication between said exit port and said rigid storage compartments; and
    iv. a sensor;
  b. placing said sample within said rigid cartridge by transferring said sample through said input port and into said rigid chamber;
  c. centrifuging said rigid cartridge such that said first portion is first urged toward said exit port by centrifugal force, directed by said valve system, and then urged toward said axis of rotation and into said first rigid storage compartment; and
  d. directing with said valve system an amount of said remaining portion toward said axis of rotation and into said second rigid storage compartment.

21. The method according to claim 20 wherein said valve system comprises a cam and flexible conduit.

22. The method according to claim 20 wherein said sensor is an optical sensor.

23. The method according to claim 20 further comprising tracking with said sensor the movement of said first portion through said exit port.

24. The method according to claim 20 wherein said rigid chamber further comprises a small end and wherein said exit port is positioned at said small end.

25. The method according to claim 20 further comprising stratifying said sample thereby generating at least one interface.

26. The method according to claim 25 further comprising detecting said at least one interface with said sensor.

27. The method according to claim 25 wherein said stratifying step generates a first and second interface.

28. The method according to claim 27 further comprising detecting said first and second interface with said sensor.

29. The method according to claim 28 wherein said directing step occurs after said sensor detects said first interface.

30. The method according to claim 28 wherein said directing step occurs after said sensor detects said second interface.

31. The method according to claim 30 further comprising tracking with said sensor the movement of said first portion through said exit port.

32. The method according to claim 20 further comprising the steps of:
  e. decelerating said rigid cartridge from a G force higher than 10 to a G force of approximately 1 G subsequent to said centrifuging step and wherein:
    i. a substantial majority of said first portion is in said first rigid storage compartment; and
    ii. a substantial majority of said remaining portion is in said rigid chamber;
  f. mixing said remaining portion through agitation of said rigid cartridge; and
  g. returning said rigid cartridge to a G force greater than 1 G for subsequent processing.

33. The method according to claim 32 further comprising tracking with said sensor the movement of said first or second portion through said exit port.

34. The method according to claim 33 wherein said sensor is an optical sensor.

35. The method according to claim 34 wherein said optical sensor comprises at least one infrared emitter/detector pair.

36. A method for depleting at least one of red blood cells, granulocytes, or platelets from a sample comprising blood, bone marrow, or stromal vascular fraction cells separated from adipose tissue, the method comprising:
 a. providing a rigid cartridge comprising:
  i. a rigid outer shell;
  ii. a generally funnel shaped internal rigid chamber having a small end comprising an output opening and a large end comprising an input opening;
  iii. a first and second rigid storage compartment initially not in fluid communication with said small end;
  iv. a first valve in communication with said output opening and said first rigid storage compartment, wherein said first valve is initially closed; and
  v. a second valve in communication with said output opening and said second rigid storage compartment, wherein said second valve is initially closed;
 b. providing a centrifuge configured to accept said rigid cartridge;
 c. providing said sample comprising a mixture of high density cells, low density cells, platelets and plasma;
 d. transferring said sample into said rigid cartridge via said input opening;
 e. placing said rigid cartridge in said centrifuge;
 f. applying centrifugal force to urge said sample towards said small end;
 g. stratifying said sample such that a substantial majority of said high density cells form a high density component layer and a substantial majority of said low density cells form a low density component layer; and
 h. opening said first valve such that said component layers migrate toward said small end and wherein said substantial majority of said high density cells are urged by centrifugal force to flow first away from said axis of rotation and then toward said axis of rotation and into said first rigid storage compartment.

37. The method according to claim 36 wherein the first valve is activated by a cam.

38. The method according to claim 36 wherein said first rigid storage compartment comprises a first rigid storage compartment input port positioned closer to said axis of rotation than said output opening, and wherein said high density cells flow through said first rigid storage compartment input port.

39. The method according to claim 36 further comprising detecting with a sensor the presence of at least one of said component layers in said small end.

40. The method according to claim 36 further comprising detecting with a first and a second sensor the presence of said component layers passing through said small end.

41. The method according to claim 40 further comprising closing said first valve and opening said second valve such that said substantial majority of said low density cells and plasma are urged by centrifugal force to flow first away from said axis of rotation and then toward said axis of rotation and into said second rigid storage compartment.

42. The method according to claim 41 further comprising the step of prior to opening said second valve, predetermining a final volume of low density cells and plasma to be added to said second rigid storage compartment.

43. The method according to claim 42 further comprising:
 i. calculating an amount of time after the detecting step that said second valve shall remain open in order to fill said second rigid storage compartment with plasma such that a final volume is substantially equal to said predetermined final volume; and
 j. closing said second valve after said amount of time.

44. The method according to claim 43 wherein said calculating step is based on an elapsed time between detection of one of said component layers by said first sensor and said second sensor.

45. The method according to claim 38 further comprising:
 k. removing centrifugal force after said opening step;
 l. agitating said rigid cartridge to mix said low density cells, said platelets and said plasma after said removing step; and
 m. reapplying centrifugal force for additional processing of said low density cells, said platelets and said plasma.

46. The method according to claim 38 wherein said high density component layer comprises red blood cells and wherein said low density component layer comprises white blood cells.

47. The method according to claim 46 wherein said low density component layer further comprises mononuclear cells.

48. The method according to claim 46 wherein said low density component layer further comprises granulocytes.

49. The method according to claim 46 wherein said high density component layer further comprises granulocytes.

50. A method for harvesting a substantially pure solution of at least one cell type from a biological fluid sample comprising high density cells, low density cells, platelets and plasma, the method comprising:
 a. providing a rigid cartridge comprising:
  i. a generally funnel shaped internal rigid chamber having a first and second exit port, said ports initially closed; and
  ii. at least two rigid storage compartments;
 b. placing a said sample comprising high density cells, low density cells within said rigid chamber;
 c. centrifuging said rigid cartridge such that a substantial majority of said high density cells form a high density component layer and a substantial majority of said low density cells form a low density component layer; and
 d. during said centrifuging step:
  i. opening said first exit port allowing passage of a portion of said high density component layer;
  ii. closing said first exit port; and
  iii. opening said second exit port allowing passage of a portion of said low density component layer.

51. The method according to claim 50 wherein one of said component layers is urged by centrifugal force to flow first through one of said exit ports and away from an axis of rotation and then toward said axis of rotation and into one of said rigid storage compartments.

52. The method according to claim 50 wherein said sample comprises at least one of blood, bone marrow, or stromal vascular fraction cells separated from adipose tissue.

53. A method for harvesting mononuclear cells from a sample of blood, bone marrow, or stromal vascular fraction cells separated from adipose tissue wherein all steps occur within a single rigid cartridge, the method comprising:
 a. providing a centrifuge having an axis of rotation;
 b. providing said rigid cartridge comprising an internal rigid chamber;

c. placing said sample into said rigid chamber, the sample comprising at least two biological components selected from the group of red blood cells, granulocytes, mononuclear cells, stem cells, platelets and plasma;
d. inserting said rigid cartridge into said centrifuge;
e. supplying with said centrifuge a centrifugal force to said sample, said centrifugal force:
   i. firstly displacing a majority of said red blood cells in said sample away from said axis of rotation, out of said rigid chamber, toward said axis of rotation, and into a first rigid storage compartment; and
   ii. secondly displacing a majority of said mononuclear cells in said sample away from said axis of rotation, out of said rigid chamber, toward said axis of rotation, and into a second rigid storage compartment.

54. The method of claim 53 wherein said internal rigid chamber has a variable radius, said radius being largest at a location proximate said axis of rotation and smallest at a location distal to said axis of rotation.

55. The method of claim 54 wherein during said secondly displacing step a majority of said mononuclear cells are concentrated in a stratified layer that increases in thickness as said stratified layer moves away from said axis of rotation.

56. A method for selectively depleting cells of differing densities from a sample, the method comprising:
a. placing a rigid cartridge within a centrifuge, said rigid cartridge comprising a rigid chamber having an end fluidly connected to a valve system comprising at least one valve which is initially closed, and at least one rigid storage compartment;
b. putting said sample in said rigid chamber, said sample comprising cells of relatively high and low density and a fluid;
c. centrifuging said rigid cartridge such that said sample is urged towards said end by a first G force;
d. centrifuging said rigid cartridge such that said sample is urged towards said end by a second G force lower than said first G force and providing an open pathway through said valve system for at least a portion of said cells of relatively high density through said end and to said at least one rigid storage compartment;
e. tracking a migration of said at least a portion of said cells through said end; and
f. closing said open pathway.

* * * * *